US007125958B1

(12) United States Patent
Wahlgren et al.

(10) Patent No.: US 7,125,958 B1
(45) Date of Patent: Oct. 24, 2006

(54) MALARIA POLYPEPTIDES

(75) Inventors: Mats Wahlgren, Stocksund (SE); Antonio Barragan, Huddinge (SE); Johan Carlson, Stockholm (SE); Chen Qijun, Stockholm (SE); Victor Fernandez, Stockholm (SE)

(73) Assignee: Karolinska Innovations AB, Stockholm (SE)

( * ) Notice: Subject to any disclaimer, the term of this patent is extended or adjusted under 35 U.S.C. 154(b) by 0 days.

(21) Appl. No.: 09/508,967

(22) PCT Filed: Sep. 18, 1998

(86) PCT No.: PCT/SE98/01675

§ 371 (c)(1),
(2), (4) Date: Apr. 7, 2000

(87) PCT Pub. No.: WO99/15557

PCT Pub. Date: Apr. 1, 1999

(30) Foreign Application Priority Data

Sep. 19, 1997 (SE) .................................. 9703386

(51) Int. Cl.
*C07K 1/00* (2006.01)
*C07K 14/00* (2006.01)
*C07K 17/00* (2006.01)
*A61K 39/00* (2006.01)
*A61K 39/002* (2006.01)
*A61K 39/015* (2006.01)

(52) U.S. Cl. ................ 530/350; 424/191.1; 424/265.1; 424/268.1; 424/272.1

(58) Field of Classification Search ............ 530/387.1, 530/300; 435/7.22; 536/23.1; 424/184.1, 424/192.1, 265.1, 266.1, 268.1, 272.1, 276.1
See application file for complete search history.

(56) References Cited

U.S. PATENT DOCUMENTS

| 5,472,953 | A | * | 12/1995 | Ekre et al. | |
| 5,849,306 | A | * | 12/1998 | Sim et al. ................. | 424/268.1 |
| 5,911,991 | A | * | 6/1999 | Pogo et al. ............... | 424/185.1 |
| 5,993,827 | A | * | 11/1999 | Sim et al. | |
| 6,120,770 | A | * | 9/2000 | Adams et al. | |
| 6,392,026 | B1 | * | 5/2002 | Sim et al. .................. | 536/23.5 |
| 6,673,601 | B1 | * | 1/2004 | Jacob et al. .............. | 435/320.1 |
| 6,855,323 | B1 | * | 2/2005 | Scherf et al. ............ | 424/272.1 |
| 6,962,987 | B1 | * | 11/2005 | Sim et al. .................. | 536/23.5 |
| 2002/0169305 | A1 | * | 11/2002 | Sim et al. .................. | 536/23.2 |
| 2004/0062769 | A1 | * | 4/2004 | Scherf et al. ............ | 424/151.1 |
| 2005/0239730 | A1 | * | 10/2005 | Mayer et al. .................. | 514/44 |
| 2006/0088501 | A1 | * | 4/2006 | Chaudhuri ................. | 424/85.1 |

FOREIGN PATENT DOCUMENTS

| WO | WO 96/30026 | 10/1996 |
| WO | WO 96/33736 | 10/1996 |
| WO | WO 96/40766 | 12/1996 |
| WO | WO 96/40766 A2 | * 12/1996 |
| WO | WO 02/12292 A2 | * 2/2002 |

OTHER PUBLICATIONS

Rowe, et al, "*P. Falaparum* Rosetting Mediated . . . " Letters to Nature vol. 388: 292-295, 1997.*
Helmby, et al, "Rosetting *Plasmodium falaparum* . . . " Infection and Immunity, 61(1): 284-288, 1993.*
Mayer et al, PNAS USA, Feb. 24, 2004, 101/8:2518-2523.*
Ikenoue et al, Southeast asian J. Trop. Med. Public Health, 2002, 33/Suppl 3: 8-13 Abstract Only.*
Costa et al, J. Infectious Diseases, Jul. 1, 2003, 188/1:153-164 Abstract Only.*
Kraemer et al, Molecular and Biochemical Parasitology, 2003, 129:91-102.*
Tami et al, Malaria Journal, 2003, 2:7.*
Tsuji et al, Biol. Chem., Apr. 2001, 382/4:553-570 Abstract Only.*
Graves et al, Cochran Database Syst. Rev., 2003, 1:CD0000129 Abstract Only.*
Kirchgatter et al, Exp. Parasitology, 2000, 95: 154-157.*
Noviyanti et al, Molecular and Biochemical Parasitology, 2001, 114:227-237.*
Smith et al, TRENDS in Parasitology, Nov. 2001, 17/11:538-545.*
Smith et al, Molecular and Biochemical Parasitology, 2000, 110:293-310.*
Ramasamy, Parasitology Today, 1998, 14/6:250.*
Haldar, Current Opinion in Microbiology, 1998, 1:466-471.*
Barragan et al, Blood, Jun. 2000, 95/11:3594-3599.*
Bouharoun-Tayoun et al, Experimental Parasitology, 2004, 108:47-52.*
Taylor-Robinson et al, J. Protozool. Research, 2001, 11:1-18.*
Shi et al, PNAS, USA, Feb. 1999, 96:1615-1620.*
Ballou et al, Am. J. Trop. Med. Hyg., 2004, 71/Suppl. 2:239-247.*
Moorthy et al, The Lancet, Jan. 10, 2004, 363:150-156.*
Joshi et al, Infection and Immunity, Jan. 2000, 68/1:141-150.*
Cox, Nature, 1992, 360:417-418.*
Kurtis et al, TRENDS in Parasitology, May 2001, 17/5:219-223.*
Kurtis et al, Infection and Immunity, Jul. 1999, 67/7:3424-3429.*
Arevalo-Herrera et al, Molecular Immunology, 2001, 38:443-455.*

(Continued)

*Primary Examiner*—Nita Minnifield
(74) *Attorney, Agent, or Firm*—Young & Thompson

(57) ABSTRACT

The present invention relates to carbohydrates capable of acting as receptors for malaria antigens present on the surfaces of malaria infected erythrocytes. The receptors according to the invention comprises negatively charged glycosaminoglycan-like moities, preferably sulphated. The invention also relates to novel malaria polypeptides capable of acting as ligands in relation to the receptors according to the invention. The invention also encompasses the use thereof as medicaments, pharmaceutical compositions containing the same as well as antibodies directed against said new ligands.

6 Claims, 6 Drawing Sheets

OTHER PUBLICATIONS

Ntumniga et al, Molecular and Biochemical Parasitology, 2004, 137:349-353.*
Stowers et al, TRENDS in Parasitology, Sep. 2001, 17/9:415-419.*
Baruch et al, PNAS, USA, Apr. 1996, 93:3497-3502.*
Howard et al, PNAS, USA, Jul. 1983, 80:4129-4133.*
Gardner et al, PNAS, USA, Apr. 1996, 93:3503-3508.*
Q. Chen et al., "Identification of *Plasmodium falciparum* erythrocyte membrane protein 1 (PfEMP1) as the rosetting ligand of the malaria parasite *P. falciparum*", *J. Exp. Med.*, vol. 187, No. 1, Jan. 1998, pp. 15-23.
S. Rogerson et al., "Sulfated glycoconjugates as disrupters of *Plasmodium falciparum* erythrocyte resoettes", *Am. J. Trop. Med. Hyg.*, vol. 5, No. 2, 1994, pp. 198-203.

* cited by examiner

Rosetting rate (%)  84  9

Trypsin  -  +

SEQUENCE LISTING

```
<160> NUMBER OF SEQ ID NOS: 10

<210> SEQ ID NO 1
<211> LENGTH: 2228
<212> TYPE: PRT
<213> ORGANISM: Plasmodium falciparum
<220> FEATURE:
<221> NAME/KEY: BINDING
<222> LOCATION: (79)..(86)
<221> NAME/KEY: BINDING
<222> LOCATION: (102)..(107)
<221> NAME/KEY: BINDING
<222> LOCATION: (201)..(207)
<221> NAME/KEY: BINDING
<222> LOCATION: (221)..(232)
<221> NAME/KEY: BINDING
<222> LOCATION: (341)..(350)
<221> NAME/KEY: BINDING
<222> LOCATION: (377)..(382)
<221> NAME/KEY: BINDING
<222> LOCATION: (411)..(418)
<221> NAME/KEY: BINDING
```

```
<222> LOCATION: (533)..(549)
<221> NAME/KEY: BINDING
<222> LOCATION: (569)..(576)
<221> NAME/KEY: BINDING
<222> LOCATION: (646)..(651)
<221> NAME/KEY: BINDING
<222> LOCATION: (688)..(693)
<221> NAME/KEY: BINDING
<222> LOCATION: (941)..(949)
<221> NAME/KEY: BINDING
<222> LOCATION: (1032)..(1039)
<221> NAME/KEY: BINDING
<222> LOCATION: (1152)..(1159)
<221> NAME/KEY: BINDING
<222> LOCATION: (1170)..(1175)
<221> NAME/KEY: BINDING
<222> LOCATION: (1232)..(1239)
<221> NAME/KEY: BINDING
<222> LOCATION: (1771)..(1777)

<400> SEQUENCE: 1

Met Ala Thr Ser Gly Gly Ser Gly Gly Thr Gln Asp Glu Asp Ala Lys
 1               5                  10                  15

His Val Leu Asp Glu Phe Gly Gln Lys Val His Asp Glu Val His Gly
            20                  25                  30

Glu Ala Lys Asn Tyr Val Ser Glu Leu Lys Gly Ser Leu Ser Leu Ala
        35                  40                  45

Ser Ile Leu Gly Glu Thr Ala Phe Thr Val Lys Ser Met Gln Thr Glu
    50                  55                  60

Ser Lys Tyr Thr Glu Leu Ile Glu Ala Asn Ser Lys Arg Asn Pro Cys
65                  70                  75                  80

Lys Lys Asp Gly Lys Gly Asn Asp Val Asp Arg Phe Ser Val Lys Glu
                85                  90                  95

Gln Ala Gly Tyr Asp Asn Lys Lys Met Lys Cys Ser Asn Gly Met Thr
           100                 105                 110

Cys Ala Pro Phe Arg Arg Leu His Leu Cys Asn Lys Asn Phe Pro Asn
       115                 120                 125

Met Asn Ser Asn Asp Ser Ser Lys Ala Lys His Asp Leu Leu Ala Glu
   130                 135                 140

Val Cys Met Ala Ala Lys Tyr Glu Gly Glu Ser Ile Lys Thr His Tyr
145                 150                 155                 160

Pro Lys Tyr Asp Ser Lys Tyr Pro Gly Ser Asp Phe Pro Met Cys Thr
                165                 170                 175

Met Leu Ala Arg Ser Phe Ala Asp Ile Gly Asp Ile Ile Arg Gly Arg
            180                 185                 190

Asp Leu Tyr Leu Gly Asn Lys Lys Lys Gln Asn Gly Lys Glu Thr
        195                 200                 205

Glu Arg Glu Lys Leu Glu Gln Lys Leu Lys Glu Ile Phe Lys Lys Ile
    210                 215                 220

His Asp Asn Leu Lys Asp Lys Glu Ala Gln Lys Arg Tyr Asn Gly Asp
225                 230                 235                 240

Glu Asp Pro Asn Phe Tyr Lys Leu Arg Glu Asp Trp Trp Thr Ala Asn
                245                 250                 255

Arg Glu Thr Val Trp Gly Ala Met Thr Cys Ser Lys Glu Leu Asp Asn
            260                 265                 270

Ser Ser Tyr Phe Arg Ala Thr Cys Asn Asp Thr Gly Gln Gly Pro Ser
        275                 280                 285

Gln Thr His Asn Lys Cys Arg Cys Asp Lys Asp Lys Gly Ala Asn Ala
    290                 295                 300
```

-continued

```
Gly Lys Pro Lys Ala Gly Asp Gly Asp Val Thr Ile Val Pro Thr Tyr
305                 310                 315                 320
Phe Asp Tyr Val Pro Gln Tyr Leu Arg Trp Phe Glu Trp Ala Glu
            325                 330                 335
Asp Phe Cys Arg Lys Lys Lys Lys Leu Glu Asn Leu Glu Lys Gln
                340                 345                 350
Cys Arg Gly Lys Asp Lys Ser Asp Glu Tyr Arg Tyr Cys Ser Arg Asn
            355                 360                 365
Gly Tyr Asp Cys Glu Gln Thr Ile Ser Arg Lys Gly Lys Val Arg Met
            370                 375                 380
Gly Lys Gly Cys Thr Asp Cys Phe Phe Ala Cys Gly Ser Tyr Glu Asn
385                 390                 395                 400
Trp Ile Asp Asn Gln Arg Lys Gln Phe Asp Lys Gln Lys Lys Tyr Thr
                405                 410                 415
Lys Glu Ile Ser Asp Gly Gly Arg Lys Arg Ala Val Gly Gly
                420                 425             430
Thr Thr Lys Tyr Glu Gly Tyr Glu Lys Ser Phe Tyr Glu Lys Leu Lys
            435                 440                 445
Asn Asp Gly Tyr Gly Thr Val Asp Ala Phe Leu Gly Leu Leu Asn Asn
450                 455                 460
Glu Lys Ala Cys Lys Asp Ile Thr Asp Gly Gly Lys Ile Asn Phe Lys
465                 470                 475                 480
Glu Val Asn Ser Gly Gly Gly Val Val Gly Gly Ser Gly Gly Thr
                485                 490                 495
Ser Gly Ala Ser Gly Thr Asn Asp Glu Asn Lys Gly Thr Phe Tyr Arg
            500                 505                 510
Ser Glu Tyr Cys Gln Pro Cys Pro Asp Cys Gly Val Gln His Lys Gly
            515                 520                 525
Gly Asn Gln Trp Glu Arg Lys Thr Lys Val Lys Met Arg Trp Ser
530                 535                 540
Lys Leu Tyr Lys Pro Ile Asn Gly Lys Met Val Leu Leu Lys Ser
545                 550                 555                 560
Leu Lys Val Val Lys Asp Met Met Ile Leu Lys Lys Asn Trp Lys Glu
                565                 570                 575
Phe Cys Leu Thr Gln Asn Ser Ser Asp Gly Ser Val Gly Ser Val Val
            580                 585                 590
Thr Thr Gly Ala Ser Gly Gly Asn Ser Glu Lys Lys Glu Leu Tyr Asp
            595                 600                 605
Glu Trp Lys Cys Tyr Lys His Asn Glu Val Gln Lys Val Asn Val Gln
610                 615                 620
Gly Glu Val Glu Glu Asp Asp Asp Glu Leu Lys Gly Ala Gly Gly Leu
625                 630                 635                 640
Cys Ile Leu Pro Asn Pro Lys Lys Asn Lys Glu Val Ser Glu Ala Lys
                645                 650                 655
Ser Gln Asn Asn His Ala Asp Ile Gln Lys Thr Phe His Asp Phe
            660                 665                 670
Tyr Tyr Trp Val Ala His Met Leu Lys Asp Ser Ile His Trp Arg Thr
            675                 680                 685
Lys Arg Leu Lys Ser Cys Ile Ser Asp Gly Lys Thr Met Lys Cys Arg
            690                 695                 700
Asn Gly Cys Asn Lys Lys Cys Asp Cys Phe Glu Lys Trp Val Lys Gln
705                 710                 715                 720
Lys Glu Thr Glu Trp Lys Pro Ile Lys Asp His Phe Lys Thr Gln Glu
```

-continued

```
              725                 730                 735
Gly Ile Pro Glu Gly Tyr Tyr Phe Thr Thr Leu Glu Leu Ile Leu Lys
            740                 745                 750
Leu Gln Phe Leu Lys Glu Asp Thr Glu Asn Thr Glu Asn Ser Leu
            755                 760                 765
Asp Ala Glu Glu Ala Glu Glu Leu Lys His Leu Gln Lys Ile Leu Lys
            770                 775                 780
Leu Glu Asn Glu Asn Asn Leu Ala Val Val Asn Ala Gly Thr Glu Gln
785                 790                 795                 800
Lys Thr Leu Met Asp Lys Leu Leu Asn His Glu Leu Asn Asp Ala Thr
                805                 810                 815
Lys Cys Lys Asp Cys Pro Leu Pro Glu Glu Asp Lys Ser Arg Gly Arg
                820                 825                 830
Ser Ala Asp Pro Ser Pro Asp Ile Phe Ile Pro Arg Pro Glu Glu Lys
                835                 840                 845
Glu Asp Asp Glu Asn Glu Asp Asp Glu Asp Val Arg Asp Asp
                850                 855                 860
Glu Glu Thr Ala Lys Glu Thr Thr Glu Gly Ser Ala Thr Asp Thr Thr
865                 870                 875                 880
Thr Ser Leu Asp Val Cys Pro Ile Val Gly Lys Val Leu Thr Lys Asp
                885                 890                 895
Asn Glu Ser Leu Gln Asp Ala Cys Ser Leu Lys Tyr Gly Gly Asn Asn
                900                 905                 910
Ser Arg Leu Gly Trp Arg Cys Val Thr Pro Ser Gly Glu Pro Thr Thr
                915                 920                 925
Ser Ser Asp Lys Asn Gly Ala Ile Cys Val Pro Pro Arg Arg Arg Arg
                930                 935                 940
Leu Tyr Ile Lys Lys Ile Val Asp Trp Ala Thr Lys Thr Glu Ser Pro
945                 950                 955                 960
Gln Ala Ser Gly Ser Glu Ala Ser Ser Thr Ser Gly Ser Thr Thr Pro
                965                 970                 975
Pro Asp Ser Lys Glu Ala Leu Leu Lys Ala Phe Val Glu Ser Ala Ala
                980                 985                 990
Ile Glu Thr Phe Phe Leu Trp His Arg Tyr Lys Glu Glu Lys Lys Ala
                995                 1000                1005
Val Ala Gln Glu Gly Ala Gly His Gly Leu Pro Arg Val Glu Glu Gly
            1010                1015                1020
Ser Pro Glu Tyr Asp Pro Glu Asp Lys Leu Lys Glu Gly Lys Ile Pro
1025                1030                1035                1040
Asp Gly Phe Leu Arg Gln Met Phe Tyr Thr Leu Gly Asp Tyr Arg Asp
                1045                1050                1055
Ile Leu Phe Ser Gly Ser Asn Asp Thr Thr Ser Val Ser Lys Asp Thr
                1060                1065                1070
Pro Ser Ser Ser Asn Asp Asn Leu Lys Asn Ile Val Leu Leu Ala Ser
                1075                1080                1085
Gly Ser Thr Glu Gln Glu Arg Glu Lys Met Asn Lys Tyr Lys Glu Ile
            1090                1095                1100
Lys Asn Phe Arg Lys Cys Ser Thr Glu Arg Ser Ala Pro Asn Leu Val
1105                1110                1115                1120
Ser His Pro Gln Thr Trp Trp Glu Asn Asn Gly Lys Tyr Ile Trp His
                1125                1130                1135
Gly Met Val Cys Ala Leu Thr Ser Lys Asp Lys Ile Ala Lys Gly Val
                1140                1145                1150
```

```
Glu Lys Lys Pro Gln Lys Ile Glu Asn Pro Glu Asn Leu Trp Asp Glu
            1155                1160                1165

Ala Asn Lys Lys Pro Lys Pro Pro Gln Tyr Gln Tyr Thr Asn Val Lys
    1170                1175                1180

Leu Asp Glu Asn Ser Gly Thr Ser Pro Arg Thr Thr Gln Thr Gln Ala
1185                1190                1195                1200

Ser Ser Asp Asn Thr Pro Thr Thr Leu Thr His Phe Val Lys Arg Pro
        1205                1210                1215

Thr Tyr Phe Arg Trp Phe Glu Glu Trp Gly Glu Ser Phe Cys Arg Glu
            1220                1225                1230

Arg Lys Lys Arg Leu Lys Gln Ile Lys Val Asp Cys Lys Val Glu Asn
        1235                1240                1245

Gly Asp Val Gly Arg Cys Ser Gly Asp Gly Glu Ala Cys Asp Ser Ile
    1250                1255                1260

Ser Thr His Asp Tyr Ser Thr Val Pro Ser Phe Asn Cys Pro Gly Cys
1265                1270                1275                1280

Gly Lys His Cys Ser Ser Tyr Arg Lys Trp Ile Glu Arg Lys Lys Ile
            1285                1290                1295

Glu Phe His Lys Gln Ser Asn Ala Tyr Gly Gln Gln Lys Thr Asp Ala
        1300                1305                1310

Thr Arg Asn Asn Gly Asn Thr Phe Asp Lys Glu Phe Cys Lys Thr Leu
    1315                1320                1325

Glu Thr Trp Pro Asp Ala Ala Lys Phe Leu Glu Arg Leu Lys Asn Gly
    1330                1335                1340

Pro Cys Lys Thr Asn Lys Glu Tyr Gly Gly Asp Asp Ile Asp Phe Glu
1345                1350                1355                1360

Lys Asp Ser Lys Thr Phe Gln His Thr Glu Tyr Cys Gly Pro Cys Pro
            1365                1370                1375

Lys Phe Lys Thr Asn Cys Gln Asn Gly Asn Cys Gly Val Ser Gly Leu
        1380                1385                1390

Asn Gly Asn Cys Asp Gly Asp Lys Ser Ile Asp Ala Lys Glu Ile Ala
    1395                1400                1405

Lys Met Arg Ser Ser Thr Thr Asp Val Val Met Arg Val Ser Asp Asn
    1410                1415                1420

Asp Thr Asn Thr Phe Glu Gly Asp Asp Leu Lys Asp Ala Cys Gln His
1425                1430                1435                1440

Ala Asn Ile Phe Lys Gly Ile Arg Lys Asp Val Trp Lys Cys Gly Tyr
            1445                1450                1455

Val Cys Gly Val Asp Ile Cys Glu Gln Thr Asn Ile Asn Glu Arg Thr
        1460                1465                1470

Asp Gly Lys Glu Tyr Ile Gln Ile Arg Ala Leu Phe Lys Arg Trp Val
    1475                1480                1485

Glu Asn Phe Leu Glu Asp Tyr Asn Lys Ile Asn Asp Lys Ile Ser His
    1490                1495                1500

Cys Ile Lys Lys Gly Glu Gly Ser Lys Cys Ile Asn Gly Cys Glu Lys
1505                1510                1515                1520

Asn Ser Lys Cys Leu Glu Lys Trp Ile Glu Lys Lys Ile Ala Glu Trp
            1525                1530                1535

Glu Asn Ile Lys Lys Arg Phe Asn Asp Gln Tyr Glu Asn Lys Asp Gln
        1540                1545                1550

Pro Asp Tyr Asn Val Lys Ser Ile Leu Glu Glu Leu Ile Pro Lys Ile
    1555                1560                1565
```

-continued

```
Ala Val Val Asn Asp Gln Asp Asn Val Ile Lys Leu Cys Val Phe Glu
    1570                1575                1580

Asn Ser Lys Gly Cys Thr Leu Ile Ser Asn Thr Gln Asn Asn Lys Glu
1585                1590                1595                1600

Asn Asp Ala Ile Asp Cys Met Leu Lys Lys Leu Gly Val Lys Ala Lys
            1605                1610                1615

Asn Cys Pro Gly Lys Pro Ser Gly Glu Lys Gln Ser Asp Cys Lys Glu
            1620                1625                1630

Pro Pro Pro Leu Pro Asp Glu Glu Asp Gln Asn Pro Glu Glu Asn Thr
        1635                1640                1645

Leu Glu Pro Pro Lys Phe Cys Pro Pro Thr Thr Gln Pro Pro Glu Glu
    1650                1655                1660

Lys Gly Gly Glu Thr Cys Gly Asn Lys Glu Glu Lys Lys Asp Glu Lys
1665                1670                1675                1680

Lys Glu Glu Ser Glu Glu Pro Ala Lys Glu Glu Ser Gly Pro Ala Ala
            1685                1690                1695

Glu Glu Pro Ala Pro Thr Ala Glu Ser Glu Glu Thr Glu Thr Asn Phe
        1700                1705                1710

Pro Glu Pro Pro Gly Thr Gly Pro Ala Ala Pro Pro Ser Thr Pro Ala
    1715                1720                1725

Pro Pro Thr Pro Asp Thr Pro Pro Pro Leu Arg Pro Gln Ala Asp Glu
    1730                1735                1740

Pro Phe Asp Ser Thr Ile Leu Gln Thr Thr Ile Pro Phe Gly Val Ala
1745                1750                1755                1760

Leu Ala Leu Gly Ser Ile Ala Phe Leu Phe Leu Lys Lys Lys Thr Lys
            1765                1770                1775

Ala Ser Val Gly Asn Leu Phe Gln Ile Leu Gln Ile Pro Lys Ser Asp
        1780                1785                1790

Tyr Asp Ile Pro Thr Leu Lys Ser Ser Asn Arg Tyr Ile Pro Tyr Val
    1795                1800                1805

Ser Asp Arg Tyr Lys Gly Lys Thr Tyr Ile Tyr Met Glu Gly Asp Ser
    1810                1815                1820

Asp Glu Asp Lys Tyr Ala Phe Met Ser Asp Thr Thr Asp Val Thr Ser
1825                1830                1835                1840

Ser Glu Ser Glu Tyr Glu Glu Leu Asp Ile Asn Asp Ile Tyr Val Pro
            1845                1850                1855

Gly Ser Pro Lys Tyr Lys Thr Leu Ile Glu Val Val Leu Glu Pro Ser
        1860                1865                1870

Gly Asn Asn Thr Thr Ala Ser Gly Lys Asn Thr Pro Ser Asp Thr Arg
    1875                1880                1885

Asn Asp Ile Gln Asn Asp Gly Ile Pro Ser Ser Lys Ile Thr Asp Asn
    1890                1895                1900

Glu Trp Asn Gln Leu Lys Lys Glu Phe Ile Ser Asn Met Leu Gln Asn
1905                1910                1915                1920

Gln Pro Asn Asp Val Pro Asn Asp Tyr Thr Ser Gly Asn Ser Ser Thr
            1925                1930                1935

Asn Thr Asn Ile Thr Thr Thr Ser Arg His Asn Val Asp Asn Asn Thr
        1940                1945                1950

Asn Thr Thr Met Ser Arg Asp Asn Met Glu Glu Asn Leu Leu Leu Pro
    1955                1960                1965

Ser Ile His Asp Gly Asn Leu Tyr Ser Gly Glu Glu Tyr Ser Tyr Asn
    1970                1975                1980

Val Asn Met Val Asn Ser Met Asn Asp Ile Pro Ile Asn Arg Asp Asn
```

-continued

```
Asn Val Tyr Ser Gly Ile Asp Leu Ile Asn Asp Ser Leu Ser Gly Gly
1985                1990                1995                2000
Lys Pro Ile Asp Ile Tyr Asp Glu Val Leu Lys Arg Lys Glu Asn Glu
        2005                2010                2015
Leu Phe Gly Thr Glu Asn Thr Lys Arg Thr Ser Thr Gln Asn Val Ala
2020                2025                2030
        2035                2040                2045
Lys Thr Thr Asn Ser Asp Pro Ile His Asn Gln Leu Glu Leu Phe His
    2050                2055                2060
Lys Trp Leu Asp Arg His Arg Asp Met Cys Glu Lys Trp Lys Asn Lys
2065                2070                2075                2080
Glu Asp Ile Leu Asn Lys Leu Lys Glu Glu Trp Asn Lys Glu Asn Ile
        2085                2090                2095
Asn Asn Ser Gly Lys Thr Tyr Asn Ser Asp Asn Lys Pro Ser His Asn
            2100                2105                2110
His Val Leu Asn Thr Asp Val Ser Ile Gln Ile Asp Met Asp Asn Pro
        2115                2120                2125
Lys Thr Lys Asn Glu Ile Thr Asn Met Asp Thr Asn Gln Asp Lys Ser
    2130                2135                2140
Thr Met Asp Thr Ile Leu Asp Asp Leu Glu Lys Tyr Asn Asp Pro Tyr
2145                2150                2155                2160
Tyr Tyr Asp Phe Tyr Glu Asp Asp Ile Ile Tyr His Asp Val Asp Val
            2165                2170                2175
Glu Lys Ser Ser Met Asp Asp Ile Tyr Val Asp His Asn Asn Val Thr
        2180                2185                2190
Ser Asn Asn Met Asp Val Pro Thr Lys Met His Ile Glu Met Asn Ile
    2195                2200                2205
Val Asn Asn Lys Lys Glu Ile Phe Glu Glu Glu Tyr Pro Ile Ser Asp
    2210                2215                2220
Ile Trp Asn Ile
2225

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Degenerate
      primer

<400> SEQUENCE: 2
ggwgcwtgyg cwccwtwymg                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Degenerate
      primer

<400> SEQUENCE: 3
arrtaytgwg gwacrtartc                                                 20

<210> SEQ ID NO 4
<211> LENGTH: 24
<212> TYPE: DNA
<213> ORGANISM: Artificial Sequence
<220> FEATURE:
```

-continued

<223> OTHER INFORMATION: Description of Artificial Sequence: Primer

<400> SEQUENCE: 4
gacatgcagc aaggagcttg ataa                                  24

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
ccatctcttc atattcactt tctga                                 25

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
ctttcgactc taccatcct                                        19

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 7
ttagatattc catatatctg ata                                   23

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 8
atcgaattct gcaaaaaaga tggaaaagga a                          31

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9 gtatttttt tgtttgtcaa attg                                   24

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 10
atcgaattct ctgaaaattt attccaaa                              28

MALARIA POLYPEPTIDES

TECHNICAL FIELD

The present invention relates to carbohydrates capable of acting as receptors for malaria antigens present on the surfaces of malaria infected erythrocytes. In addition, the invention also relates to novel malaria polypeptides capable of acting as ligands in relation to the receptors according to the invention. The invention also encompasses the use thereof as medicaments and vaccines, pharmaceutical compositions containing the same as well as antibodies directed against said new ligands.

BACKGROUND AND PRIOR ART

On a worldwide basis, malaria is one of the most common infectious diseases. Even though it has been largely eliminated from North America and Europe, it remains the most serious infectious disease in tropical and subtropical regions of the world. According to the World Health Organisation, WHO, there are about 100 million new cases each year, and about 300 million people in the developing countries exhibits chronical malaria infections. Malaria is caused by four species of Plasmodium, of which Plasmodium vivax and Plasmodium falciparum are most frequently involved in human infections. The vector responsible for transmitting malaria to humans is the Anopheles mosquito and only malaria infections caused by Plasmodium falciparum may be fatal to humans.

After inoculation in the body, the sporozoites of Plasmodium begin to reproduce within liver cells. Multiplication of Plasmodium sporozoites occurs by schizogony, in which a single sporozoite can produce as many as 40,000 merozoites. The invasion of erythrocytes by hepatic merozoites begins the erythrocytic phase of malaria, causing fever and other severe manifestations.

Erythrocytes infected with the malaria parasite P. falciparum disappear from the peripheral circulation as they mature from the ring stage to trophozoites. This phenomenon is known as sequestration and results from parasitized erythrocyte adherence to microvascular endothelial cells and erythrocytes in diverse organs. Severe Plasmodium falciparum-malaria is characterized by excessive sequestration of infected- and uninfected erythrocytes in the microvasculature of the affected organ.

Thus, Plasmodium falciparum is an intracellular protozoan, which during its vertebrate life cycle invades and multiplies in liver and red blood cells. The virulence of the parasite is associated with the capacity of the infected erythrocyte to adhere to endothelial cells and to erythrocytes, so called resetting. This may cause impaired local oxygen delivery and thereby death of the human host (Miller, L. H., F. Good, and G. Milon. 1994. Malaria pathogenesis. Science 264, 1878–1883, Pasloske, B. L. and R. J. Howard. 1994. Malaria, the red cell, and the endothelium. Ann. Rev. Med. 45, 283–295, Marsh, K., M. English, J. Crawley, and N. Peshu, 1996. The pathogenesis of severe malaria in African children. Ann. Trop. Med, & Parasitol. 90, 395–402). The most malignant form of the infection is cerebral malaria, due to a massive sequestration of infected and uninfected erythrocytes in the brain micro-vasculature.

After being transported from the internal parasite, antigens involved in the binding of cells are thought to be concentrated and subsequently exposed to the exterior of the erythrocyte at minute (≈100 nm in diameter), electron-dense excrescence's called knobs (Atkinson, C. T. and M. Aikawa, 1990. Ultrastructure of malaria-infected erythrocytes. Blood Cells 16, 351–368). One such antigen is Plasmodium falciparum erythrocyte membrane protein-1 (PfEMP1), a polypeptide of 200–350 kDa encoded by the var family of P. falciparum genes (Howard, R. J., J. W. Barnwell, and V. Kao, 1983. Antigenic variation in Plasmodium knowlesi malaria: identification of the variant antigen on infected erythrocytes. Proc. Natl. Acad. Sci. U.S.A. 80, 41294133, Su, X. -Z, V. M. Heatwole, S. P. Wertheimer, F. Guinet, J. A. Herrfeldt, D. S. Peterson, J. A. Ravetch, and T. E. Wellems. 1995. The large diverse gene family var encodes proteins involved in cytoadherence and antigenic variation of Plasmodium falciparum-infected erythrocytes. Cell 82, 89–100, Baruch, D. I., B. L. Pasloske, H. B. Singh, X. Bi, X. C. Ma, M. Feldman, T. F. Taraschi, and R. J. Howard. 1995. Cloning th P. falciparum gene encoding PfEMP1, a malaria variant antigen and adherence receptor on the surface of parasitized human erythrocytes. Cell 82, 77–87). The feature of antigenic variation and switching of the surface of the pRBC has been attributed to the var-genes. Even though up to 150 such genes are harboured in the genome, only one PfEMP1 is thought to be expressed at any one time. PfEMP1 has features of an adhesive molecule and has been associated with the cytoadherent properties of the infected red cell (Smith, J. D., C. E. Chitnis, A. G. Craig, D. J. Roberts, D. E. Hudson-Taylor, D. S. Peterson, R. Pinches, C. I. Newbold, and L. H, Miller. 1995. Switches in expression of Plasmodium falciparum var genes correlate with changes in antigenic and cytoadherent phenotypes of infected erythrocytes. Cell 82, 101–110, Baruch, D. I., J. A. Gormley, C. Ma, R. J. Howard, and B. L. Pasloske. 1996. Plasmodium falciparum erythrocyte membrane protein 1 is a parasitised erythrocyte receptor for adherence to CD36, thrombospondin, and intercellular adhesion molecule 1. Proc. Natl. Acad. Sci. U.S.A. 93, 3497–3502). For example, the expression of PfEMP1-encoding var genes has been shown to correlate with the capacity of the pRBC for binding to host receptors, including CD36 and ICAM-1 (Baruch, D. I., J. A. Gormley, C. Ma, R. J. Howard, and B. L. Pasloske. 1996. Plasmodium falciparum erythrocyte membrane protein 1 is a parasitised erythrocyte receptor for adherence to CD36, thrombospondin, and intercellular adhesion molecule 1. Proc. Natl. Acad. Sci. U.S.A. 93, 3497–3502, Gardner, J. P., R. A. Pinches, D. J. Roberts, and C. I. Newbold, (1996). Variant antigens and endothelial receptor adhesion in Plasmodium falciparum. Proc. Natl. Acad. Sci. U.S.A., 93, 3503–3508). A role for PfEMP1 in resetting was recently suggested by Rowe et al (Rowe, J. A., J. M. Moulds, C. I. Newbold, and L. H. Miller. 1997. P. falciparum resetting mediated by a parasite-variant erythrocyte membrane protein and complement-receptor 1. Nature 388:292–295). Complement receptor 1 was found to be the host-receptor. However, it is beleived that it cannot be the only one used by rosetting parasites.

In WO 96/33736, one PfEMP1 variant is disclosed by sequence. However, this is only one of several possibly existing variants, all of which are different as to functional sequences as well as adhesive properties.

Accordingly, due to the complex nature and/or mechanism of malarial antigenic variation and the virulence thereof, there is still a great need for methods and compositions which may be useful in the treatment, diagnosis and prevention of malaria infections.

OBJECT OF THE INVENTION

The present invention fulfills the need described above by providing a carbohydrate, which is useful as a receptor for malaria erythrocyte membrane protein. The invention also provides such a new malaria protein acting as a ligand in relation to the receptors according to the invention.

DEFINITIONS

Figure 1A:
FIG. 1 discloses the identification of rosetting PfEMP1.

The term "glycosaminoglycan-like" as used in the present disclosure refers to any molecule or substance, that exhibits the same or similar advantageous properties as the glycosaminoglycans comprising repeated units of sulfated or acetylated disaccharides and further discussed below.

As used herein, the term "essentially specific binding" in the context of the carbohydrates according to the invention is interpreted as such a specific binding as is needed to influence the rosetting of malaria erythrocyte membrane protein without having any other notable impact on the environment.

The terms "polypeptide", "peptide" and "protein" are used interchangeably herein to refer to a polymer of amino acid residues. The terms apply to amino acid polymers, in which one or more amino acid residue is an artificial chemical analogue of a corresponding naturally occurring amino acid, as well as to naturally occurring amino acid polymers. The terms "isolated" "purified", or "biologically pure" refer to material which is substantially or essentially free from components which normally accompany it as found in its native state.

The term "biologically active fragment" as used herein refers to portions of the proteins or polypeptides possessing a particular biological activity, e.g. one or more activities found in the full length novel PfEMP1 variant according to the invention.

The term "fusion protein" as used herein generally refers to a composite protein made up of two or more separate, heterologous proteins.

The term "substantial identity" or "substantial similarity" in the context of a polypeptide indicates that a polypeptides comprises a sequence with at least 70% sequence identity to a reference sequence, or most preferably 80%, or more preferably 85 sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

A "conservative substitution", when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. (See, e.g., Creighton (1984) *Protein*, W.H. Freeman and Company.) In addition, individual substitutions, deletions or additions which alter, add or delete a single amino acid or a small percentage of amino acids in an encoded sequence are also "conservatively modified variations".

An indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions, as discussed in more detail below.

The term "nucleic acid" refers to a deoxyribonucleotide or ribonucleotide polymer in either single- or double-stranded form, and unless otherwise limited, encompasses known analogues of natural nucleotides that can function in a similar manner as naturally occurring nucleotides.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point Tm for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents, such as formamide.

As used herein a "nucleic acid probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, C, or T) or modified bases (7-deazaguanosine, inosine, etc.) In addition, the bases in a probe may be joined by a linkage other than a phosphodiester bond, so long as it does not interfere with hybridization. Thus, for example, probes may be peptide nucleic acids in which the constituent bases are join d by peptide bonds rather that phosphodiester linkages. It will be understood by one of skill in the art that probes may bind target sequences lacking complete complementarity with the probe sequence depending upon the stringency of the hybridization conditions. The probes are preferably directly labelled as with isotopes, chromophores, lumiphore, chromogens, or indirectly labelled such as with biotin to which a streptavidin complex may later bind, By assaying for the presence or absence of the probe, one can detect the presence or absence of the select sequence or subsequence.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in a ELISA), biotin, dioxigenin, or haptens and proteins for which antisera or monoclonal antibodies are available (e.g., the peptide of the invention can be made detectable, e.g., by incorporating a radio-label into the peptide, and used to detect antibodies specifically reactive with the peptide).

A "labelled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The term "target nucleic acid" refers to a nucleic acid (often derived from a biological sample), to which a nucleic acid probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the ovarall sequence (e.g., gene or mRNA) whose expression level it is desired to detect. The difference in usage will be apparent from context.

"Bind(s) substantially" refers to complementary hybridization between a probe nucleic acid and a target nucleic acid and embraces minor mismatches that can be acc modated by reducing the stringency of the hybridization media to achieve the desired detection of the target polynucleotide sequence.

"Subsequence" refers to a sequence of nucleic acids or amino acids that comprise a part of a longer sequence of nucleic acids or amino acids (e.g., polypeptide), respectively.

In the present disclosure, the term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu alpha, delta, or epsilon, which in turn define the immunoglobulin classes, IgG, IgM, IgA, IgD and IgE, respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that utilizes an antibody to specifically bind an analyte. The immunoassay is characterized by the use of specific binding properties of a particular antibody to isolate, target, and/or quantity the analyte.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbour Publications, New York, for a description of immunoassay formats and conditions that can be used to determine specific immunoreactivity.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all. The term "identical" in the context of two nucleic acids or polypeptide sequences refers to the residues in the two sequences which are the same when aligned for maximum correspondence. Optimal alignment of sequences for comparison can be conducted, e.g., by the local homology algorithm of Smith and Waterman (1981) *Adv. Appl. Math,* 2:482, by the homology alignment algorithm of Needleman and Wunsch (1970) *J. Mol. Biol.* 48:443, by the search for similarity method of Pearson and Lipman (1988) *Proc. Natl. Acad. Sci. USA* 85:2444, by computerized implementations of these algorithms (CAP, CESTFIT, FASTA, and TFASTA in the Wisconsin Genetics Software Package, Genetics Computer Group, 575 Science Dr., Madison Wis.) or by inspection. An additional algorithm that is suitable for determining sequence similarity is the BLAST algorithm, which is described in Altshul et al. (1990) *J. Mol. Biol.* 215: 403–410. Software for performing BLAST analyses is publicly available through the National Center for Biotechnology Information.

DETAILED DESCRIPTION OF THE PRESENT INVENTION

The present invention is disclosed in more detail below. All references throughout the present application are hereby included herein by references.

Thus, in a first aspect, the present invention relates to a carbohydrate, which exhibits at least one negatively charged glycosaminoglycan-like moiety and thereby is capable of essentially specific binding to a malaria erythrocyte membrane protein or an analogue thereof. Accordingly, the carbohydrate according to the invention may be used as a receptor to bind ligands, which are expressed on the surface of cells infected by malaria, such as erythrocytes infected by *Plasmodium falciparum*. In a preferred embodiment, said glycosaminoglycan moiety is sulfated and more specifically, it may be a heparan sulfate moiety. Most preferably, the carbohydrate according to the invention is fucoidan, or a functional fragment thereof. Further, the invention also relates to any functionally equivalent analogues of the above described carbohydrates.

Indeed, it has been shown in the prior art that *P. falciparum*-rosettes may be disrupted by low concentrations of heparin, an effect that is immediate and reversible (Carlson, J., H. P. Ekre, H. Helmby, J. Gysin, B. M. Greenwood, and M. Wahlgren. 1992. Disruption of *Plasmodium falciparum* erythrocyte rosettes by standard heparin and heparin devoid of anticoagulant activity. *Am, J. Trop. Med. Hyg.* 46, 595–602, Rowe, A., A. R. Berendt, K. Marsh, and C. I. Newbold. 1994. *Plasmodium falciparum*: a family of sulfated glycoconjugates disrupts erythrocyte rosettes. *Exp. Parasitol.* 79, 506–16). However, prior to the present invention, it has not been possible to explain the mechanism or basis for this phenomena and, accordingy, it has not been possible to create any such advantageous and useful receptors as the present receptor carbohydrate until now. Thus, for the first time, the present invention discloses receptors capable of essentially specific binding of such malaria proteins.

The glycosaminoglycans, or GAGs, being the receptor carbohydrate according to the invention, are composed of repeated units of sulfated or acetylated di-saccharides and are present in the human body bound to a protein-core in the form of proteoglycans (PG) (Yanagisha, M. and V. Hascall. 1992. Cell surface heparan sulfate proteoglycans. *J. Biol. Chem.* 267, 9451–9454). Heparan sulfate and chondroitin sulfate are GAGs exposed at all human cell-surfaces, but they are diverse and vary from cell-to-cell and maybe within the same cell due to secondary modifications of the extensive carbohydrate chains (deacetylations, O-sulfations etc.). Heparin is only found in mast-cells and is characterized by a higher degree of sulfation and epimerization than heparan sulfate. However, heparan sulfate and heparin are similar due to heparin-like stretches also found in heparan sulfate (Faham, S., E. R. Hileman, R. J. Fromm, J. R. Lindardt, and C. D. Rees. 1996. Heparin structure and interactions with basic fibroblast growth factor. *Science,* 271, 1116–1120).

HS and heparin, both members of the heterogeneous GAG family, are composed of alternating glucosamine and uronic acid residues. The glucosamine can be either N-sulfated or N-acetylated and can contain an O-sulfate ester at C-6. The uronic acid exists as either a glucoronic or an iduronic acid epimer and may be O-sulfated at C-2. In contrast to heparin chains which are extensively sulfated, HS chains are less extensively modified and the sulfate groups are unevenly distributed over the chains due to incompleteness of modification in each step of RS biosynthesis (Lindahl et al. 1994) Consequently, HS and heparin are similar due to highly sulfated, heparin-like stretches found in HS.

In general, micro-heterogeneity within the structure of GAGs modulates their binding and biological activities (Casu 1991). Their binding properties are usually associated with their anionic sulfate and carboxyl groups. Increasing charge density and molecular weight is often associated with stronger protein binding, but this is not a strict rule (Ruoslahti 1989). Thus, a general increase in binding properties can be achieved by chemical oversulfation (Casu 1991). Most GAGs express their biological properties through interactions with plasma and tissue components (Jackson et al. 1991; Kjellén et al. 1991) and their ubiquitous distribution on cell surfaces make them well suited for microbial attachment.

In a particular embodiment, the receptor carbohydrate, or said functional equivalent thereof, is more specifically capable of essentially specific binding to at least one of the segments denoted binding sites of the amino acid sequence according to SEQ ID NO:1, wherein a novel variant of *Plasmodium falciparum* erythrocyte membrane protein (PfEMP1) is disclosed. Even though it is more fully discussed elsewhere in this application, especially in connection with the ligand polypeptide below, it should be understood that said binding segments are sequences, which, according to the present invention, have been found to bind specifically and strongly to glycosaminoglycan-like moieties on receptor substances, such as the ones present on most cells or the present polypeptide. Thus, in a specific embodiment, the receptor carbohydrate according to the invention is capable of binding to an amino terminal part, and preferably an essential part, of the binding segments indicated in SEQ ID NO:1. Consequently, the protein disclosed in SEQ ID NO:1 may be regarded as a ligand, whereas the carbohydrate defined as above may be regarded as the receptor therefore. Most preferably, the receptor binds to an essential part of said sequence or any sequence having a substantial identity or similarity with SEQ ID NO:1.

The carbohydrate receptor according to the present invention may be prepared by fractionation from animal cells or by conventional methods, which are well known in the art (see e.g. Binkley: *Modern Carbohydrate Chemistry*, Marcel Dekker, New York, 1988, with references; and U.S. Pat. Nos. 5,308,460 and 5,532,147).

In another aspect, the present invention relates to a carbohydrate as defined above for use as a medicament as well as the use of said receptor as a medicament. Such a medicament is effective in that it is capable of effectively dissolving the rosettes formed by erythrocytes infected by a malaria parasite, as described more detailed in the introductory section of this application. Thereby, a medicament comprising the receptor carbohydrate according to the invention in a suitable form will be effective in dissolving and preventing the occlusion of blood vessels, especially in cerebral malaria. Accordingly, the invention also encompasses the use of said carbohydrate in the manufacture of a medicament against malaria, preferably against *P. falciparum* malaria Thus, in one embodiment, the invention relates to a pharmaceutical composition comprising a carbohydrate according to the invention ill a pharmaceutically or veterinary acceptable carrier. Other additives or excipients which are deemed suitable for the specific application may also be present in such a composition. Further, the present invention also relates to any other substance, which has been achieved by use of parts or all of the novel polypeptide defined in SEQ ID NO:1, or, alternatively, by use of a carbohydrate according to the invention as a lead substance, for use as medicaments, for use in the manufacture of pharmaceutical preparations and pharmaceutical compositions comprising such a substance together with a carrier. Methods for producing such substances, which are functionally equivalent to the present carbohydrates, will be discussed in more detail below.

One more aspect relating to the above defined carbohydrate, or malaria protein receptor substance, is a method of treating a patient suffering from a malaria infection, preferably a *P. falciparum* infection. Such a method comprises administering to the patient of an effective amount of the pharmaceutical composition described in detail elsewhere in the present description.

Another aspect of the present invention is a polypeptide, which is capable of acting as a ligand in relation to the receptor carbohydrate described above. Said ligand polypeptide originates from a malaria erythrocyte membrane protein and may be denoted a novel PfEMP1-variant.

Thus, by single-cell RT-PCR, the present inventor has identified a novel PfEMP1-variant of a resetting parasite. Clusters of GAG-binding motifs have been identified in the sequence, denoted binding sites in the sequence listing below. In addition, it has been shown that the recombinant form of the novel PfEMP1-variant, or ligand polypeptide, according to the invention, adheres to solid-phase heparin, to heparan sulfate on the erythrocyte surface, and disrupts rosettes. Further, naturally formed rosettes also seem to be mediated by binding to the same GAG.

In an advantageous embodiment, the ligand polypeptide according to the invention comprises at least about 300 amino acids of the amino acid sequence according to SEQ ID NO:1. Preferably, the ligand comprises an amino terminal sequence of said sequence, or an analogue thereof. More preferably, the ligand according to the invention comprises about 400–500 amino acids, and most preferably about 400 amino acids (DBL-1), such as about 423 amino acids, thereof. In addition, the ligand polypeptide according to the invention is capable of essentially specific binding to a negatively charged glycosaminoglycan-like moiety. In the preferred embodiment thereof, the ligand polypeptide according to the invention is capable of binding any receptor carbohydrate according to the invention and described above, In a particular embodiment thereof, the polypeptide according to the invention comprises essentially all of the sequence according to SEQ ID NO:1, wherein the complete amino acid sequence of FCR3S1.2 PfEMP1 is shown. The location of potential GAG binding motifs are shown in pink. Motifs no. 4, 5 and 9, 10 (aa 221–232 and 533–549, respectively) are seen as a single stretch as they are located next to each other (see methods section for description of identification of GAG-binding motifs). These sequence data are available from GenBank under accession number of AF003473.

The weight of the polypeptide according to the invention will depend on the length of the amino acid sequence as discussed above but may be about 100–300 kDa, preferably about 280 kDa. Further, the present invention also relates to any biologically active fragments of the herein disclosed polypeptides and proteins.

Another aspect of the invention is a method of pr paring a ligand polypeptide as defined herein, which comprises the steps of
(1) the inserting into an expression vector of a nucleic acid encoding said ligand polypeptide or functionally equivalent analogue thereof;
(2) the transfection of a host cell capable of expressing said nucleic acid with said expression vector to express said polypeptide; and
(3) the recovery of the expressed polypeptide and advantageously purification thereof to a biologically pure form. Expression vectors, host cells, process parameters etc. are easily chosen by someone skilled in this area.

Accordingly, a further aspect of the invention is vectors on host cells useful in the above disclosed method and comprising nucleic acids encoding a polypeptide according to the invention.

In one particular embodiment of the invention, the polypeptide may be cloned using DNA amplification methods, such as the polymerase chain method (PCR) (see e.g. Sambrook et al., *Molecular Cloning: A Laboratory Manual*, 2$^{nd}$ ed., Cold Spring Harbour, N.Y., 1989; Berger & Kiel, *Methods in Enzymology*, Vol. 152: *Guide to Molecular Cloning Techniques*, Academic Press, Inc., San Diego, Calif., 1987; Co et al (1992) *J. Immunol.* 148:1149). Thus, for example, the nucleic acid sequence, which will be disclosed in more detail below, or subsequence is PCR amplified using a sense primer containing one restriction site and an antisense primer containing another restriction site. This will produce a nucleic acid encoding the desired sequence or subsequence having terminal restriction sites. This nucleic acid can then easily be ligated into a vector having appropriate corresponding restriction sites. Suitable PCR primers are easily chosen by one of skill in the art based on the sequence to be expressed. Appropriate restriction sites can also be added by site-directed mutagenesis (see Gillman & Smith (1979) *Gene*, 8: 81–97; Roberts et al. (1987) *Nature* 328: 731–734).

The nucleic acids according to the invention, which are described in more detail below, may be expressed in a variety of host cells, including *E. coli*, other bacterial hosts, yeast and various higher eucaryotic cells, such as the COS, CHO and HeLa cell lines and myeloma cell lines. The recombinant protein gene will be operably linked to appropriate expression control sequences for each host. For *E. coli*, this includes a promoter, such as the T7, trp, or lambda promoters, a ribosome binding site and preferably a transcription termination signal. For eucaryotic cells, the control sequences will include a promoter and preferably an enhancer derived from immunoglobulin genes, SV40, cytomegalovirus etc., and a polyadenylation sequence, and may include splice donor and acceptor sequences. The plasmids can be transferred into the chosen host cell by well-known methods, such as calcium chloride transformation for *E. coli* and calcium phosphate treatment or electroporation for mammalian cells. Cells transformed by the plasmids can be selected by resistance to antibiotics conferred by genes contained on the plasmids, such as amp, gpt, neo and hyg genes.

Once expressed, the recombinant polypeptides according to the invention may be purified according to standard procedures of the art, including ammonium sulfate precipitation, affinity columns, column chromatography, gel electrophoresis and the like (see generally R. Scopes, *Protein Purification*, Springer-Verlag, N.Y. (1982), Deutcher, *Methods in Enzymology vol.* 182: *Guide to Protein Purification*, Academic Press, Inc. N.Y. (1990)). Substantially pure compositions are preferred, such as at least about 90–95% homogeneity, and most preferred, 98–99% homogeneity. Once purified, partially or to the homogeneity as desired, the polypeptides according to the invention may be used, e.g. as immunogens for antibodyproduction.

As one of skill in this field would recognize, after chemical synthesis, biological expression, or purification, the proteins, polypeptides or fission proteins according to the present invention may possess a conformation substantially different from the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see e.g. Debinski et al. (1993) *J. Biol. Chem.*, 268; 14065–14070; Kreitman and Pastan (1993) *Bioconj. Chem.*, 4:581–585; and Buchner et al. (1992) *Anal. Biochem.*, 205:263–270).

One of skill would recognize that modifications can be made to the present polypeptides and proteins without diminishing their biological activity, e.g. in order to facilitate cloning, expression or incorporation of the targeting molecule into a fusion protein. Such modifications are well known and any thus modified peptides and proteins are understood to be encompassed within the scope of the present invention as defined by the appended claims.

Further, the present invention also relates to vectors and recombinant host cells comprising the sequence according to SEQ ID NO:1 or any biologically active fragment thereof. In addition, the invention also encompasses any isolated cell comprising the sequence according to SEQ ID NO:1 as an endogenous gene, which has been manipulated by gene activation, that is, wherein additional regulatory sequences have been introduced in order to increase the expression of the native coding sequence (see e.g. U.S. Pat. No. 5,578,461 and U.S. Pat. No. 5,641,670). The culture of cells according to the present invention is well known in the art (see e.g. Freshney, Culture of Animal Cells, A Manual of Basic Technique, third ed., Wiley-Liss, New York (1994) and the references cited therein for a general guide to the culture of cells).

As indicated above, the present invention also relates to nucleic acids encoding the polypeptides according to the invention as well as to any nucleic acid capable of specific hybridization, under stringent conditions, to such a nucleic acid. The nucleic acids according to the invention thus include, but are not limited to, DNAs, RNAs, an mRNA transcript, a cDNA reverse transcribed from a mRNA, and RNA transcribed from that cDNA, a DNA amplified from the cDNA, an RNA transcribed from the amplified DNA or subsequences of any of these nucleic acids and may be prepared by any suitable method, which is easily chosen by someone skilled in this field. Such methods include, for example, cloning and restriction of appropriate sequences or direct chemical synthesis by methods such as the phosphotriester method (Narang et al., *Meth. Enymol.* 68:90–99 (1979)); the phosphodiester method (Brown et al., *Meth. Enzymol.* 68: 109–151 (1979)); the diethylphpsphoramidite method (Beaucage et al., *Tetra. Lett.*, 22:1859–1862 (1981)); and the solid support method (U.S. Pat. No. 4,458,066).

Chemical synthesis produces a single stranded oligonucleotide. This may be converted into double stranded DNA by hybridization with a complementary sequence or by polymerisation with a DNA polymerase using the single strand as a template. The DNA sequence obtained by chemical synthesis is limited in length by the technique used, however, longer sequences are easily obtained by the ligation of such shorter sequences to the desired length. Alternatively, subsequences may be cloned and the appropriate subsequences cleaved using suitiable restriction enzymes. The fragments may then be ligated to produce DNA sequences of the desired size.

A nucleic acid according to the invention may e.g. be used in the above method for preparing a polypeptide, as a probe etc. For the use thereof as a probe, it is often desirable to label the sequence with a detectable label. The label may be incorporated during the amplification step in the preparation of the nucleic acid, e.g. by PCR, by transcription amplification using a labelled nucleotide incorporations a label in the transcribed nucleic acid or, alternatively, by direct addition thereof, such as by nick-translation or any other suitable method Detectable labels suitable for use according to the present invention include any composition detectable by spectroscopic, photochemical, biochemical, immunochemical, electrical, optical or chemical means and methods for the detection thereof are well known to those of skill in the art.

In an alternative aspect of the invention, the polypeptide is produced in the form of a recombinant fusion protein, which comprises said polypeptide, comprising suitable glycosaminglycan-like moieties, fused to another protein or polypeptide. Such a polypeptide comprising fusion protein may be more advantageous for certain applications than the polypeptide per se. In a preferred embodiment of the invention, the fusion proteins are synthesized using recombinant nucleic acid methodology. Generally, this involves creating a nucleic acid that encodes the receptor-targeted fission molecule, placing the nucleic acid in an expression cassette under the control of a suitable promoter, expressing the protein in a host, isolating the expressed protein and, if required, renaturing the protein. Techniques sufficient to guide one of skill through such procedures are found in e.g., Sambrook et al., *Molecular Cloning, A Laboratory Manual*, $2^{nd}$ ed., vol. 1–3, Cold Spring Harbor Laboratory, 1989; Berger and Kimmel, *Guide to Molecular Cloning Techniques*, Methods in Enzymology, vol. 152, Academic Press, Inc., San Diego, Calif.; and *Current Protocols in Molecular Biology*, F. M. Ausubel et al., eds., Current Protocols (Greene Publishing Associates, Inc. And John Wiley & Sons, Inc.) (1994 Supplement). Alternatively, the fusion protein is produced by any method for chemical synthesis well known in the art. Thus, a fusion protein according to the invention may comprise any polypeptide, antibody or biologically active fragment thereof according to the present invention. The effects of exemplary fusion proteins on rosetting is e.g. discussed in the Experimental section of this specification, see e.g. FIG. 4.

The present invention also relates to a polypeptide according to the invention for use as a medicament as well as the use thereof in the manufacture of a medicament. Such a medicament is effective in that it is capable of effectively dissolving the rosettes formed by erythrocytes infected by a malaria parasite, as described more detailed in the introductory section of this application. Thereby, a medicament comprising the polypeptide according to the invention, per se or in the form of a fusion protein, will be effective in dissolving and preventing the occlusion of blood vessels, esecially in cerebral malaria. In addition, the above described rosettes have also been shown to be associated with other severe complications of malaria (Carlson, J., et al, Lancet 336, 1457–1460 (1990); Treutiger et al, Am. J. Trop. Med. Hyg. 46, 503–510 (1992); and Rowe, A et al, Inf. Immun 63, 2323–2326 (1995)). Thus, a medicament comprising a polypeptide according to the invention is also effective in the treatment of such other conditions. Accordingly, the invention also encompasses the use of said polypeptide in the manufacture of a medicament against malaria, preferably *P. falciparum* malaria, and/or other severe complications of malaria. Consequently, in a further aspect, the invention relates to a pharmaceutical preparation comprising said polypeptide or fusion protein in a pharmaceutically or veterinary acceptable carrier, e.g. an aqueous carrier, such as buffered saline or the like. These solutions are sterile and generally free of any undesirable matter. They may be sterilized by conventional, well known sterilization techniques. The pharmaceutical preparations according to the invention may be used in any suitable method of administration, such as in parenteral, topical, oral or even local administration for prophylactic and/or therapeutic treatment and may be administered in a variety of unit dosage forms depending on the administration method chosen. Further, the pharmaceutical compositions according to the invention may comprise any pharmaceutically acceptable auxiliary substances required to approximate physiological conditions, such as pH adjusting and buffering agents, toxicity adjusting agents and the like, for example sodium acetate, sodium chloride, potassium chloride, calcium chloride, sodium lactate etc. Actual methods for preparing the appropriate administrable compositions will be known or apparent to those skilled in this field and are described in more detail in e.g. *Remington's Pharmaceutical Science*, 15$^{th}$ ed., Mack Publishing Company, Easton, Pa. (1980). (For a brief review of methods for drug delivery, see Langer, Science 249:1527–1533 1990)).

Accordingly, another aspect of the present invention is a method of treating a patient suffering from a malaria infection by the administration of the present polypeptide or a fusion protein or, alternatively, preventing malaria in a subject at risk of being infected thereof. It is to be understood, that in the present context, the term "preventing" refers to the prevention of a disorder, such as malaria, or the symptoms thereof, by use of a medicament as well as such a prevention by use of a vaccine composition. Thus, the present invention encompass preventive or prophylactic treatments and medicaments used therein, which treatments will include drugs that actively participate in the prevention of a particular disorder, such as malaria or the symptoms thereof. Further, the invention also encompases treatments that elicit a preventive response from a patient, such as an immunological response in the case of vaccination. Consequently, "a medicament for the prevention of malaria" includes also includes vaccine compositions. The method comprises administering to said patient of an effective amount of the herein described pharmaceutical composition, said amount being dependent on the severity of the disease and the general state of the health of the patient. Preferably, the malaria infection treated by the method according to the invention is a *P. falciparum* infection.

In the preferred embodiment, the vaccine compositions according to the invention will include a molecule according to the invention, such as a polypeptide, in an immunologically effective amount together with a suitable pharmaceutically acceptable carrier. In this context, examples of suitable carriers are e.g. thyroglobulin, albumins, such as human serum albumin, tetanus toxoid, polyamino acids, such as poly(D-lysine; D-glutamic acid), influenza, hepatitis B virus core protein as well as other carriers well known to those skilled in the art. The vaccines may also include a physiologically tolerable diluent, such as water, buffered water, buffered saline, saline and they may further also include any suitable adjuvant, such as incomplete Freunds' adjuvant, aluminium phosphate, aluminium hydroxide, alum, ammonium hydroxide in case of human pateient, etc. The immune response of the patient may include generation of antibodies, activation of cytotoxic T-lymphocytes against cells expressing the polypeptides or other mechanisms known within this field. (See e.g. Paul, *Fundamental Immunology*, 2$^{nd}$ ed., Raven Press; Sedagh et al., *Proc. Natl. Acad. Sci.* (1994) 91:9866–9877; U.S. Pat. No. 4,722,848; and Langford, C. L. et al., 1986, *Mol. Cell. Biol.* 6:3191–3199.)

Another highly interesting and advantageous aspect of the present invention is the use of the polypeptide as defined above as a model substance for identifying substances binding to a malaria erythrocyte membrane protein, such as the novel variant disclosed in SEQ ID NO:1, or analogues thereof. Thereby, new receptor substances effective in the treatment and/or prevention of malaria infections may be isolated from suitable environments or bulks comprising the same.

More specifically, a polypeptide according to the invention, or a fragment thereof is used in the design of an organic compound, which is modeled to resemble the three dimensional structure of the amino acid residues of said polypeptide. Such a design of mimetics to a known pharmaceutically active compound is a known approach to the development of pharmaceuticals based on a "lead" compound. Mimetic design, synthesis and testing is generally used to avoid randomly screening large number of molecules for a target property. In relation to mimetics, or mimics, as they are sometimes denoted, see for example Shikman A. R. and Cunningham M. W., *J. Immunol.* 152(9):4375 (1994); Vaughan et al., *Xenotransplantation* 3:18–23 (1996); and Koogman et al, Dean (1994), BioEssays, 683–687; Cohen and Shatzmiller (1993), *J. Mol. Graph.*, 11: 166–173; Wiley and Rich (1993), *Med. Res. Rev.*, 13:327–384; Moore (1994), *Trends Pharmacol. Sci.*, 15:124–129; Hruby (1993), *Biopolymers*, 33: 1073–1082; Bugg et al. (1993), Sci. Am., 269:92–98.

In brief, the particular parts of the compound that are critical and/or important are firstly determined. This can be done systematically by varying the amino acid residues in the peptide, e.g. by substituting each residue in turn. These parts or residues constituting the active region of the compound are known as its "pharmacophore". Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a specific embodiment, the three dimensional structure of the ligand and its binding partner are modelled This can be especially useful where the ligand and/or binding partner (receptor) change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable and does not degrade in vivo, while retaining the biological activity of the lead compound. The mimetic(s) found by this approach can then be screened to see whether or not they have the target property, or to what extent they exhibit it. Further optimisation or modification can then be carried out to arrive at one or more final mimetics for in vivo or clinical testing. Accordingly, the use of the present polypeptide ligand and/or carbohydrate binding partner as models to identify optimal pharmaceutically active substances, preferably for preventing and/or treating malaria, is encompassed by the present invention as are any substances identified thereby, which fulfills the herein desired criteria.

In another aspect, the invention relates to diagnostic and screening assays, wherein e.g. the polypeptides according to the invention are used for the detection of antibodies or wherein antibodies as disclosed below are used to detect PfEMP1 or fragments thereof. Further, nucleic acids may be detected in biological samples. (For a review of diagnostic immunoassay procedures, see e.g. *Basic and Clinical Immunology*, 7$^{th}$ ed., Stites, D., and Terr, A., 1991.)

One further aspect of the invention is an antibody, which is specifically immunoreactive with a ligand polypeptide according to the present invention. Such an antibody may be used to formulate another pharmaceutical composition together with suitable pharmaceutically and/or veterinary acceptable carriers, excipients etc. Accordingly, the present invention also relates to such antibody compositions as well as to methods of treating and/or preventing malaria infection in a patient. Such methods comprises administer to said patient of an effective amount of the pharmaceutical composition defined above. Most preferably, the infection to be treated and/or prevented is a *P. falciparum* infection.

Thus, antibodies are raised to the polypeptides of the present invention, including individual, ellelic, strain, or species variants, and fragments thereof, both in their naturally occurring (full-length) forms and in recombinant forms. Additionally, antibodies are raised to these polypeptides in either their native configuarions or in non-native configurations. Anti-idiotypic antibodies can also be generated. Many methods of making antibodies are known to persons of skill. (In this context, see e.g. *Fundamental Immunology*, Third Edition, W. E. Paul, ed., Raven Press, N.Y. 1993.) While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

A number of immunogens are used to produce antibodies specifically reactive with polypeptides according to the invention. Recombinant or synthetic polypeptides according to the invention of 8–15, preferably 10, amino acids in length, or greater, are the preferred polypeptide immunogen (antigen) for the production of monoclonal or polyclonal antibodies.

Methods of producing polyclonal antibodies are known to those of skill in the art. See, e.g., Coligan (1991) *Current Protocols in Immunology* Wiley/Greene, NY; and Harlow and Lan (1989) *Antibodies: A Laboratory Manual* Cold Spring Harbor Press, NY.

Monoclonal antibodies are prepared from cells secreting the desired antibody. These antibodies are screened for binding to normal or modified polypeptides, or screened for agonistic or antagonistic activity, e.g., activity mediated through a suppressor of fused protein. Specific monoclonal and polyclonal antibodies will usually bind with a $K_D$ of at least about 0.1 mM, more usually at least about 50 µM, and most preferably at least about 1 µM or better.

In some instances, it is desirable to prepare monoclonal antibodies from various mammalian hosts, such as mice, rodents, primates, humans, etc. Description of techniques for preparing such monoclonal antibodies are found in, e.g. Stites et al. (eds) *Basic and Clinical Immunology* (4th ed.) Lange Medical Publications, Los Altos, Calif., and references cited therin; Harlow and Lane, supra; Goding (1986) *Monoclonal Antiboides: Principles and Practice* (2nd ed.) Academic Press, New York, N.Y.; and Kohler and Milstein (1975) *Nature* 256: 495497.

Other suitable techniques involve selection of libraries of recombinant antibodies in phage or similar vectors (see, e.g., Huse et al. (1989) *Science* 246: 1275–1281; and Ward, et al. (1989) *Nature* 341–544-546; and Vaughan et al. (1996) *Nature Biotechnology*, 14: 309–314).

Advantageously, the polypetides and antibodies according to the invention are labelled by joining, either covalently or non-covalently, a substance which provides for a detectable signal. A wide variety of labels, and conjugation techniques are known and are reported extensively in both the scientific and patent literature. See for example patents teaching the use of such labels, including U.S. Pat. Nos. 3,817,837; 3,850,752; 3,939,350; 3,996,345; 4,277,437; 4,275,149; and 4,366,241.

In a specific embodiment of the invention, the present antibodies are used for affinity chromatography in isolating polypeptides. Columns are prepared, e.g., with the antibodies linked to a solid support, e.g., particles such as agarose, Sephadex, or the like, where a cell lysate is passed through the column, washed, and treated with increasing concentrations of a mild denaturant, whereby purified polypeptides are released.

The antibodies can be used to screen expression libraries for particular expression products. Usually the antibodies in such a procedure are labelled with a moiety allowing easy detection of presence of antigen by antibody binding.

Antibodies raised against the present polypeptides can also be used to raise antiidiotypic antibodies. These are useful for detecting or diagnosing the various pathological conditions related to the presence of the respective antigens.

The antibodies of this invention can also be administered to an organism (e.g., a human patient) for therapeutic purposes. A large numer of methods of generating chimeric antibodies are well known to those of skill in the art (see, e.g., U.S. Pat. Nos. 5,502,167, 5,500,362, 4,491,088, 5,482, 856, 5,472,693, 5,354,847, 5,292,867, 5,231,026, 5,204,244, 5,202,238, 5,169,939, 5,081,235, 5,075,431, and 4,975,369). For references regarding human antibodies, see, e.g., Larrick et al., U.S. Pat. No. 5,001,065, for review).

Human antibodies of the present invention are may e.g. be produced initially in trioma cells. The general approach for producing human antibodies by trioma technology has been described by Ostberg et al. (1983) *Hybridoma* 2: 361–367, Ostberg, U.S. Pat. No. 4,634,664, and Engelman et al. U.S. Pat. No. 4,634,666.

As someone skilled in this field easily realises, the receptor carbohydrates, the ligand polypeptide and the antibodies according to the invention are also useful for a wide variety of diagnostic purposes, such as in immuno assays. Methods, other reagents, amounts etc are easily determined by someone skilled in the area on the basis of the information given in this application (for immuno assays, see e.g. Harlow and Lane (1988) *Antibodies, A Laboratory Manual*, Cold Spring Harbour Publications, New York).

DETAILED DESCRIPTION OF THE DRAWINGS

In addition to the description given in this section, the drawings will also be commented under "Results" below.

FIG. 1. Identification of Rosetting PfEMP1.

FIG. 1A rosetting, single *P. falciparum*-infected erythrocyte is seen by light microscopy held by a 5 µm micropipette (A, 1). The uninfected erythrocytes are stripped of the infected cell and careful examination confirms that it indeed is infected by a single parasite (A, 2–3).

Figure 1B:
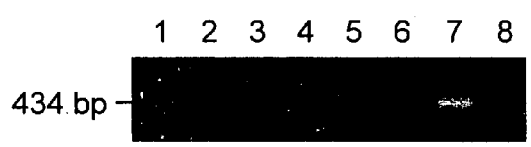

FIG. 1B shows the amplification of a 434 bp band in 4 (from reaction 3, 4, 5 and 7) out of 8 single-infected, rosetting erythrocytes using degenerate primers generated from the primary sequence of the DBL-1 domain of PfEMP1.

Figure 1C:
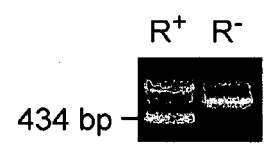

FIG. 1C shows the amplification pattern with the same primers as in B of bulk cultures of rosetting ($R^+$) FCR3S1.2 cultures and the $R^-$ FCR3s/a parasites. Note that the 434-bp product is only seen with the $R^+$ parasites.

Figure 1D:
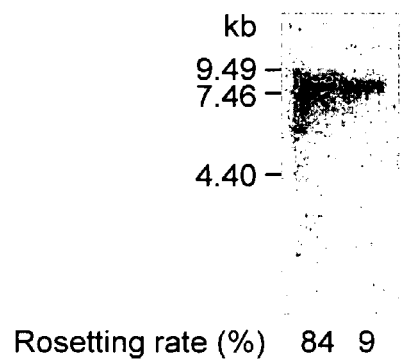

FIG. 1D shows the hybridisation pattern in Northern blotting of the 434-bp sequence to mRNA extracted from the highly rosetting parasite FCR3S1.2 (84% $R^+$) and the weak hybridisation to the $R^-$ FCR3S/a parasite (9% $R^+$).

Figure 1E:

FIG. 1E shows the autoradiogarph of a Triton-X 100 insoluble, SDS-soluble extract of FCR3S1.2 infected erythrocytes after radio-iodination labelling. PfEMP1 (arrowed) is labelled on FCR3S1.2 infected erythrocytes and is cleaved by low concentrations of trypsin.

Figure 2A:
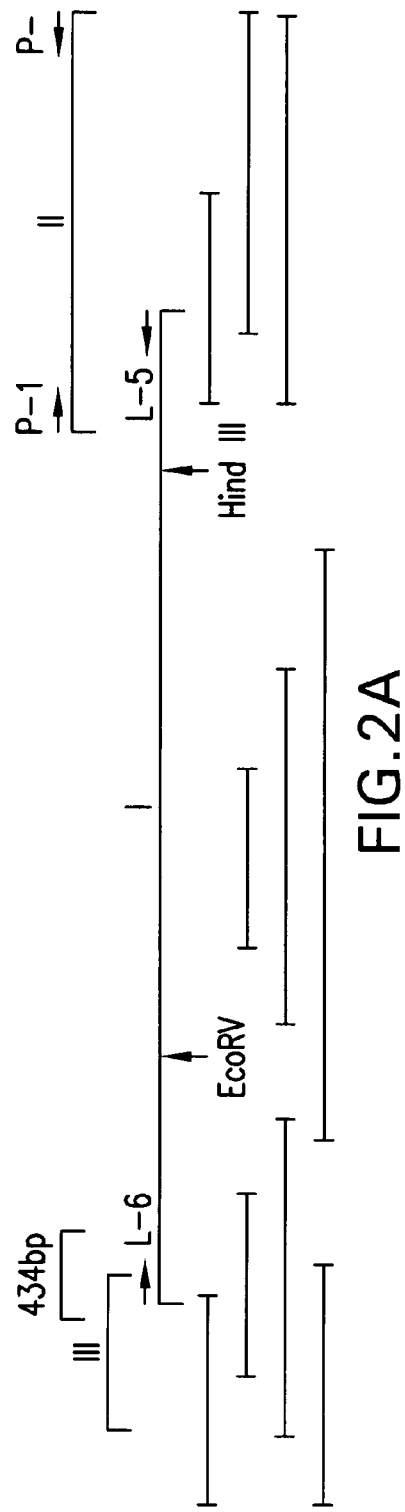
FIGS. 2A–C disclose, respectively, maps of cDNA structure, sequencing clones, deduced amino acid sequence and the location of GAG binding motifs in the rosetting PfEMP1 of FCR3S1.2.
Figure 2B:
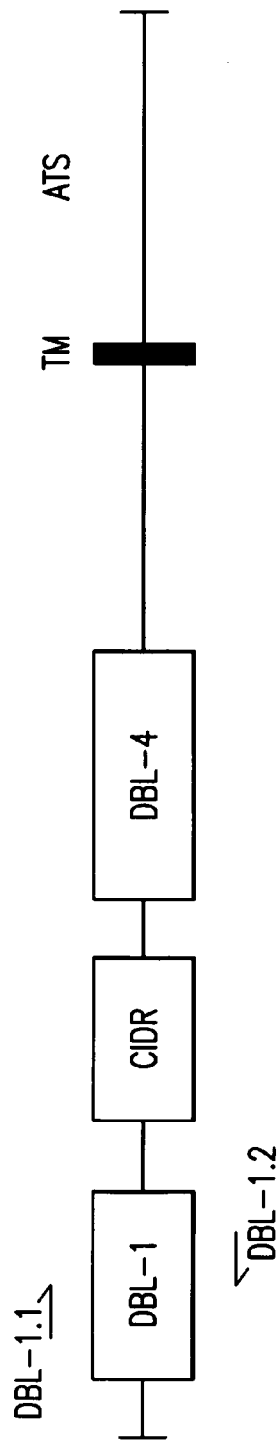
Figure 2C:

FIG. 2. Map of cDNA structure, sequencing clones, deduced amino acid sequence and the location of GAG binding motifs in the resetting PfEMP1 of FCR3S1.2. A shows the location of 434-bp fragment and the three fragments (I, II and III) which were intially cloned for sequencing. Restriction enzyme-digestion sites are indicated by arrows. Additional overlapping clones used for sequencing are shown below. B shows the primary structure of the rosetting FCR3S1.2-PfEMP1. It has two Duffy binding-like (DBL) domains (DBL-1 and 4), one cysteine-rich interdomain region (CIDR), one transmembrane (TM) region and one acidic C-terminal segment (ATS). C shows the distribution of amino acids in different regions of FCR3S1.2-PfEMP1.

FIG. 3. Rosetting FCR3S1.2-PfEMP1 binds to heparan sulfate. All the gels are 10% SDS-PAGE stained with Coomassie. A shows the expressed GST, DBL-1-GST or ATS-GST after purification on glutathione-sepharose and SDS-PAGE. B shows the binding capacity of different fission proteins to heparin-sepharose after SDS-PAGE. C shows the inhibition produced by different glycosamlnoglycans on the binding of DBL-1-GST to heparin-sepharose followed by SDS-PAGE. D & E show the binding of DBL-1-GST (D) and ATS-GST (E) to monolayers of normal RBC as visualised by a mAb to GST labelled with biotin and FITC-avidin.

Figure 4:
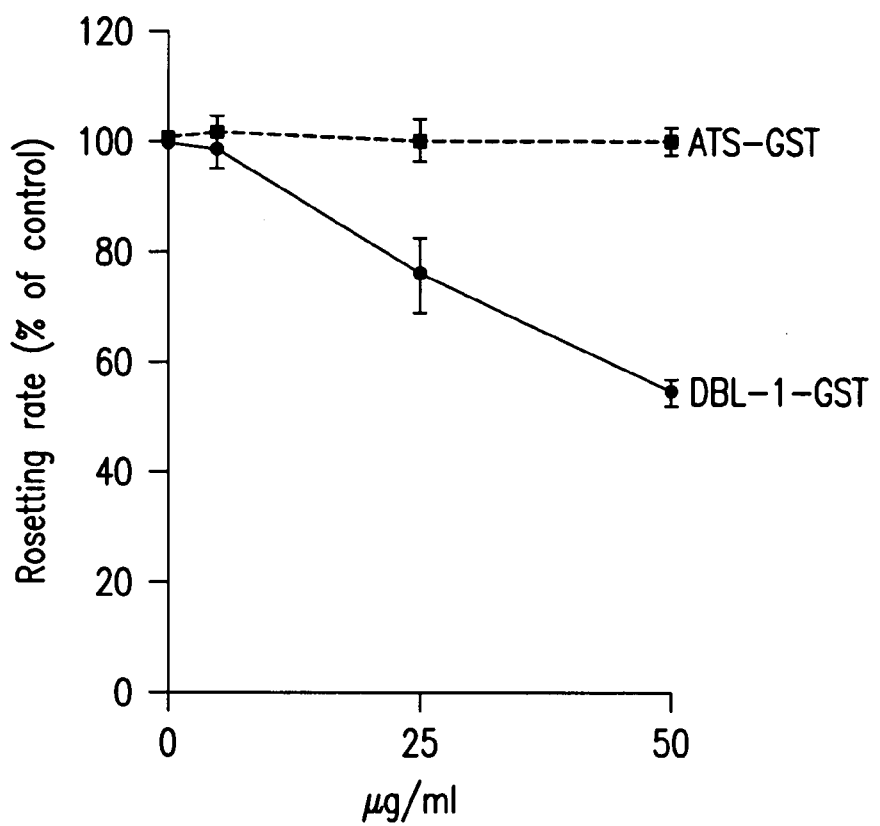
FIG. 4 discloses the disruption of preformed natural rosettes with either one of the fusion proteins DBL-I-GST or ATS-GST.

FIG. 4. Disruption of pre-formed, natural rosettes with either DBL-1-GST or ATS-GST.

Results are means and standard errors of three experiments.

FIG. 5. Effect of glycosaminoglycans (GAGS) on *P. falciparum* resetting. A shows disruption of rosettes exerted by different GAGs. FCR3S1.2 cultures were incubated with GAGs for 1 h at 37° C. and compared to control culture. Results are the means and standard error of three separate experiments. B shows the effect of enzyme treatment of uninfected, C-FDA labelled, erythrocytes in a competitive assay of rosette-reformation in the presence of normal erythrocytes and FCR3S1.2 infected pRBC, Results are the means and standard error of three separate experiments; two experiments for neuramimidase.

EXPERIMENTAL

The following examples are only intended to illustrate the present invention and do not limit the scope of the invention as defined by the appended claims. Throughout the present application, the following abbreviations are used:

PfEMP 1, *Plasmodium falciparum* erythrocyte membrane protein 1; DBL, Duffy binding-like; GST, glutathione S-transferase; GAG, glycosaminoglycan; pRBC, parasitised RBC; ICAM-1, intercellular adhesion molecule 1; TM, transmembrane.

Example 1

Materials and Methods

The Parasites

The *P. falciparum* parasites were cultured according to standard methods with 10% $AB^+$ $Rh^+$ serum added to the buffered medium (RPMI supplemented with hepes, gentamycin and sodium bicarbonate). The FCR3S1.2 was cloned with micro-manipulation from the previously limiting-dilution cloned parasite FCR3 (Udomsangpetch, R., B. Wåhlin, J. Carlson, K. Berzins, M. Torii, M. Aikawa, P. Perlmann, and M. Wahlgren. 1989. *Plasmodium falciparum-infected* erythrocytes form spontaneous erythrocyte rosettes. *J. Exp. Med.* 169, 1835–1840). Its rosetting rate was routinely >80% ($R^+$). FCR3S/a was negatively enriched for low rosetting from FCR3 using Ficoll-isopaque (<10%, $R^-$). It should be noted that FCR3S was previously called Palo Alto (Uganda) in our publications (Carlson, J., H. P. Ekre, H. Helmby, J. Gysin, B. M. Greenwood, and M. Wahlgren. 1992. Disruption of *Plasmodium falciparum* erythrocyte rosettes by standard heparin and heparin devoid of anticoagulant activity. *Am. J. Trop. Med. Hyg.* 46,595–602, Udomsangpetch. R., B. Wåhlin, J. Carlson, K. Berzins, M. Torii, M. Aikawa, P. Perlmann, and M. Wahlgren. 1989. *Plasmodium falciparum-infected* erythrocytes form spontaneous erythrocyte rosettes. *J. Exp. Med.* 169, 1835–1840, Scholander, C., C. J. Treutiger, K Hultenby, and M. Wahlgren. 1996. Novel fibrillar structure confers adhesive property to malaria-infected erythrocytes. *Nature Med.* 2, 204–208, Carlson, J. and M. Wahlgren, 1992. *Plasmodium falciparum* erythrocytes resetting is mediated by promiscuous lectin-like interactions. *J. Exp. Med.* 176, 1311–1317, Carlson, J., G. Holmquist, D. W. Taylor, P. Perlmann, and M. Wahlgren. 1990. Antibodies to a histidine-rich protein (PfHRP1) disrupt spontaneously formed *Plasmodium falciparum* erythrocyte rosettes. *Proc. Natl. Acad. Sci. U.S.A* 87, 2511–2515, Helmby, H., L. Cavelier, U. Pettersson, and M. Wahlgren. 1993. Rosetting *Plasmodium falciparum*-infected erythrocytes express unique antigens on their surface. *Infect. Immun.* 61, 284–288). Molecular studies of the "Palo Alto" parasites have revealed, however, that they are identical to parasites of the FCR3 lineage (Fandeur, T., S., O. Bonnefoy, Mercereau-Puijalon. 1991. In vivo and in vitro derived Palo Alto lines of *Plasmodium falciparum* are genetically unrelated. *Mol. Biochem. Parasitol.* 47, 167–178).

Optimisation of Single *P. falciparum* RT-PCR

Two degenerate primers (DBL-1.1, 5'-GG(A/T) GC(A/T) TG(TC) GC(A/T) CC(A/T) T(A/T) (T/C) (A/C) G-3' (SEQ ID NO: 2); DBL-1.2, 5'-A(A/G)(A/G)T A(T/C)TG (T/A)GG (A/T)AC (A/G)TA (A/G)TC-3' (SEQ ID NO: 3) which mapped to the conserved region of all PfEMP1 DBL-1 were modified from the sequences of Su et al. The amplification parameters were first optimised so that the amplified products were visible with normal ethidium bromide (EB) staining (Cobb, B. D. and J. M. Clarkson, 1994. A simple procedure for optimising the polymerase chain reaction (PCR) using modified Taguchi methods, *Nucl. Acid. Res.* 22, 3801–3805). Briefly, one to five parasites, obtained by limiting dilution, were directly emerged in the RT-PCR buffer (Stratagene) with different concentration of primers, $MgCl$ KCl and Tris-Cl. Both DNA and RNA were released from the parasites by heating at 93° C. for 3 min. The DNA was degraded by addition of 10 U DNase (Stratagene). Reverse transcription was carried out immediately after the addition of random primers and reverse transcriptase (Perkin-Elmer). The PCR reaction was subsequently performed in the same tube. Through comparison of the amplification efficiency from different reactions, the optimised parameters for single cell RT-PCR were found to be as follows: 100 mM Tris-Cl, pH 8.3, 35 mM $MgCl_2$, 500 mM KCl, and the final concentration of primers was 1 μM. In the subsequent experiments, individual trophozoite-infected resetting erythrocytes were isolated with a 5 μM glass-pipette using an inverted microscope. The selected pRBC was stripped of uninfected RBC and repeatedly grabbed, ejected and turned to conclusively ensure that it had pigment and that the selected cell was a single trophozoite-infected RBC (see FIG. 1A). Fifty cycles of amplification at 93° C. for 20 seconds, 55° C. for 30 seconds and 72° C. for 1 min were needed for product detection. Several controls were included in each experiment; one blank control (without parasite(s)) and one without reverse-transcriptase to rule out the possibility of contamination and amplification due to the presence of genomic DNA.

RT-PCR with Total RNA from Bulk-Cultured FCR3S1.2 or FCR3Sa and Northern-Blot Analysis Total RNA purification from both FCR3S1.2 (R$^+$) and FCR3S/a (R$^-$) parasite and RT-PCR was performed as described (Sambrook, J., E. F., Fritsch, and T., Maniatis. 1989. Molecular Cloning, A laboratory manual, second edition. Cold Spring Harbor Laboratory Press). All the amplified products were cloned with Original TA Cloning Kit (Invitrogen) and sequenced, Northern blot analysis was carried out using standard methods (Sambrook, J., E. F., Fritsch, and T., Maniatis. 1989. Molecular Cloning, A laboratory manual, second edition. Cold Spring Harbor Laboratory Press). Membranes were probed overnight at 60° C. using the 434-bp fragment labelled with a-$^{32}$p-dCTP. Washing was performed under stringent conditions (60° C., 0.1×SSC) and the blots were examined in a Molecular Dynamics phosphoimager.

Cloning and Sequencing of the Whole cDNA

A specific upstream primer (L-6, 5'-GAC ATG CAG CAA GGA GCT TGA TAA-3') (SEQ ID NO: 4) in the 434-bp sequence and a downstream primer (L-5, 5'-CCA TCT CTT CAT ATT CAC TTT CTG A-3') (SEQ ID NO: 5) mapping to the conserved sequence of ATS were generated and reverse transcription was carried out as described above. PCR was performed with the Expand™ High Fidelity PCR System (Boehringer Mannheim). A single 4.9-kb fragment was amplified, which was digested into three fragments with Hind III and EcoR V and cloned into the pZErO-1 vector (Zero Background, Invitrogen). The sequencing was performed with LongRanger™ gel (FMC) on an A.L.F. Sequencer (Pharmacia). The 5' region of the FCR3S1.2-var1 transcript was cloned by screening a cDNA library (Schlichtherle, unpublished) with the 434-bp fragment as probe and seven overlapping fragments were sequenced. The 3' terminal region was cloned by nested RT-PCR. Reverse transcription was primed with oligo-dT and PCR was performed with a specific 5' primer (P-1, 5'-CTT TCG ACT CTA CCA TCC T-3') (SEQ ID NO: 6) upstream of TM region and a 3' primer (P-4, 5'-TTA GAT ATT CCA TAT ATC TGA TA-3') (SEQ ID NO: 7) mapping to the C-terminal sequence of FCR3 (var 2) PfEMP 1. Five overlapping fragments were sequenced. Fourteen overlapping clones were in total sequenced in both directions in order to ensure that the sequence was correct and was transcribed from a single gene.

Sequence Analysis

The DNA and amino acid sequence analysis (editing, translation, peptidesort, plot, etc.) was performed with the Genetic Computer Group (GCG) (Devereux, J., P. Haeberli, and O. Smithies. 1984 A comprehensive set of sequence analysis programs for VAX. *Nucl. Acid. Res.* 12, 387–395) program. Alignment of the deduced amino acid sequence with the published PfEMP1 sequences in the GenBank was made to identify the sequence. The identification of potential GAG-binding motifs in FCR3S1.2-var1 and in the other published PfEMP1 sequences was done by firstly searching for the presence's of either of the 4 amino-acid motifs KK, KR, RK, or RR, and secondly manually checking each of the identified sequences for the presence of the motifs XBBXBX or XBBBXXBX where B is a basic amino acid (K, R, H) and X is a hydropathic residue. A certain degree of liberty concerning the location of the basic residues in the motifs is acceptable (Cardin, A. D. and H. J. R. Weintraub, 1989. Molecular modeling of protein-glycosaminoglycan interactions. *Arteriosclerosis* 9, 21–32).

Expression of DBL-1 or ATS Using the pGEX-4T-1 Vector

Both DBL-1 and ATS fragments were amplified by specific primers (Ex-1.1, 5'-ATC GAA TTC TGC AAA AAA GAT GGA AAA GGA A-3' (SEQ ID NO: 8) and D-1, 5'-GTA TTT TTT TTG TTT GTC AAA TTG-3' (SEQ ID NO: 9) for DBL-1; Ex-2, 5'-ATC GAA TTC TCT GAA AAT TTA TTC CAA A-3' (SEQ ID NO: 10) and P-4 for ATS). The amplified fragments were inserted into the EcoR I cloning site of pGEX-4T-1 downstream of the glutathione S-transferase sequence. The *E. coli* BL21 was used as the expression strain. Expression of both fusion proteins was induced with 0.1 mM IPTG at 30° C. for 4 h and the fusion proteins were purified on glutathione sepharose (Pharmacia) as described in the instructions provided by the manufacturer (GST Gene Fusion System, Pharmacia). The expression constructs were sequenced by cycle sequencing to check that the recombinant plasmids were of the expected sequences in the correct reading frames. Thrombin cleavage of the fusion proteins was performed according to a standard procedure. Western-blot analysis of DBL-1-GST and ATS-GST fusion proteins was with a biotin labelled anti-GST mAb (clone GST-2, IgG2b, Sigma) and ALP-avidin (Sigma) to reveal the pattern of protein expression. Although the induction of expression was at a low temperature and the purification was in the presence of a cocktail of enzyme inhibitors (0.5 mM EDTA, 1 mM PEFABLOC (serine protease inhibitor) (AEBSF) Boehringer Mannheim), there was still some breakdown of the DBL-1-GST. The fusion proteins, stained by the anti-GST mAb, decreased with thrombin treatment. This information together with the knowledge that the plasmids were of the expected sequences ensured that the fusion proteins indeed were the corrected ones.

Heparin Binding and Blocking Assay

The potential binding of the fusion proteins to heparin was studied by mixing either DBL-1-GST, ATS-GST fusion protein or GST alone (20 µl, 150 µg/ml in PBS) with 20 µl of 50% heparin-sepharose (Pharmacia) and incubating for 5 min at room temperature in the absence of serum; binding to uncoupled sepharose was used as control. The heparin-sepharose and protein mixture was washed 3 times in large volumes of PBST buffer (PBS plus 0.05% Tween-20) before extracting bound proteins in loading-buffer for 10% SDS-PAGE. Inhibition of DBL-1-GST fission protein binding to heparin with heparin, heparan sulfate or chondroitin sulfate (Lövens Kemiske Fabrik, Denmark, more than 90% pure) was also tested. Twenty µl of 150 µg/ml DBL-1-GST fusion protein was mixed separately for 5 minutes with an equal volume of heparin, heparan sulfate, or chondroitin sulfate, titrated from 10 to 0.5 mg/ml, before the addition of heparin sepharose. The inhibitory activities were checked by SDS-PAGE.

Erythrocyte Binding and Blocking Assay

Ten-well immunofluorescence glass-slides were pre-coated with 10% poly-L-lysine in PBS for 30 min. Monolayers of RBC were made by addition of 20 µl of 0.5% 3× washed bloodgroup O Rh+RBC in PBS to each well. Twenty µl DBL-1-GST, ATS-GST or GST alone (80 µg/ml) in PBS was added to the wells for 30 min. The DBL-1-GST fusion protein was in subsequent experiments incubated in the presence of heparin, heparan sulfate or chondroitin sulfate (titrated from 20 to 8 mg/ml) to study the inhibitory activity of each GAG. Slides were washed 3 times with PBS and the fusion protein-binding was detected with the biotin-labelled anti-GST mAb and an EXTRAVIDIN (a modified avidin) FITC conjugate (Sigma). The fluorescence was assessed in a Nikon Optiphot-2 UV microscope, using a ×10 ocular and an oil lens with a magnification of ×100.

Rosette Disruption Assay

The assay was performed essentially as described (Carlson, J. and M. Wahlgren, 1992. *Plasmodium falciparum* erythrocytes resetting is mediated by promiscuous lectin-like interactions. *J. Exp. Med.*, 176, 1311–1317). The recombinant fission proteins (25 ml in PBS of DBL-1-GST or ATS-GST) were added to 25 µl aliquots of a ≈80% rosetting culture of FCR3S1.2 in a micro-titre plate. The mixtures were incubated for 30 min. at 37° C. after which the rosetting rate was scored and compared to mock treated controls after staining with acridine orange.

Enzyme Treatment of Normal RBC

Human bloodgroup O Rh+ erythrocytes (5% suspension in RPMI) were, previous to C-FDA labelling (Carlson, J., G. Holmquist, D. W. Taylor, P. Perlmann, and M. Wahlgren. 1990. Antibodies to a histidine-rich protein (PfHRP1) disrupt spontaneously formed *Plasmodium falciparum* erythrocyte rosettes. *Proc. Natl. Acad. Sci U.S.A* 87, 2511–2515), incubated for 60–90 min with either heparinase III (25° C., pH 7.5; Sigma), chondroitinase ABC (37° C., pH 8.0; Sigma) or with *C. perfringens* neuraminidase (37° C., pH 6.0; Sigma). Cells were washed three times after treatment and resuspended in complete malaria medium, with 10% serum. Control erythrocyte suspensions were mock treated, washed and incubated as above.

Results

Identification of a Novel Rosetting PfEMP1-Variant

With the aim of identifying and isolating a PfEMP1-variant of a rosetting parasite, a single-cell RT-PCR assay was developed using micro-manipulation. Since the PfEMP1 messages are mostly expressed at ring stage, it is a difficult task to amplify cDNA from single trophozoites. However, the present inventor was successful in four out of eight pRBC studied and, when amplified, it was always a 434-bp sequence that was found (FIG. 1B). This was confirmed by amplification of var transcripts from bulk cultures, where the 434 bp amplificate was again detected unique to the resetting *P. falciparum* and was not found present in non-rosetting parasites (FIG. 1C). Both the single cell- and the RT-PCR with the total RNA from the bulk cultures were repeated several times to make sure that the results were reproducible. Further, the 434-bp product was also found present in 7 out of 12 ring stage-parasites using single-cell RT-PCR (data not shown). Sequence analysis revealed that the amplified product encoded the semi-conserved sequence of the 5' located DBL-I domain of the var genes. Ten 434-bp sequences obtained from separate amplifications were found to be identical. 9 distinct PCR-amplified var transcripts from non-rosetting parasites were also isolated subcloned and sequenced. They were in all instances different from the 434-bp sequence (not shown). Northern-blot analysis with mRNA from the FCR3S1.2 clone and the 434-bp sequence as the labelled probe revealed a transcript of about ≈7.5-kb, the difference with the size of the coding cDNA of 6.7 kb being accounted for by a relatively larg untranslated 5' region (Sundström et al, unpublished. The weak hybridisation seen with mRNA from R-parasites is probably due to hybridyzation to a different transcript (FIG. 1D). Thus, according to the present invention, a unique PfEMP1 transcript has been found in rosetting parasites.

cDNA Structure of Rosetting PfEMP1

The entire coding region of the var-transcript containing the 434-bp motif was assembled with the 13 overlapping fragments and the coding sequence was found to be composed of 6684-bp (SEQ ID NO:1). 6684-bp encodes a 2228 aa polypeptide with an estimated molecular weight of 260 kDa. A single trypsin-sensitive polypeptide of a similar size was seen after $^{125}$I-lactoperoxidase surface-labelling of the FCR3S1.2 FIG. 1E).

In an in-depth analysis of the expressed FCR3S1.2-var1 transcript, it was found that the overall structure was similar to the published var-sequences, However, the sequence of the novel variant according to the present invention differs substantially from the prior sequences in that it is shorter than most previous sequences, as it contains two DBL-domains (DBL-1 and 4), rather than four, separated by a cysteine-rich interdomain region (CIDR) (FIG. 2B). Both the TM region and the negatively charged, acidic C-terminal segment (ATS) of the FCR3S1.2-var1 exhibited a certain degree of homology (≈80%) to previously published sequences. However, neither the potentially variable sequences of 434-bp var-gene fragment nor the other regions of the cDNA were contained in other published var-sequences, such as the one described in WO 96/33736.

Rosetting PfEMP1 Contains Clusters of Glycosaminoglycan-Binding Motifs

The FCR3S1.2-var1 sequence was examined for the presence of potential GAG-binding motifs. 19 potential GAG-binding sequences were identified and it was found that ≈95% of them (18/19) were located in the N-terminus. 8/19 were situated in DBL-1, 5/19 in the CIDR C-terminally to DBL-1 and 5/19 in DBL-4. Only one potential GAG-binding motif was seen beyond the TM region (SEQ ID NO:1). The N-terminal distribution of these aa clusters is therefore consistent with the accessibility of the FCR3S1.2-var1 at the surface of the pRBC. Thus, this may be the molecular background to rosetting and thereby explain why rosettes are sensitive to heparin.

Rosetting PfEMP1 Binds to a Heparan Sulfite-Like GAG

Figure 3C:
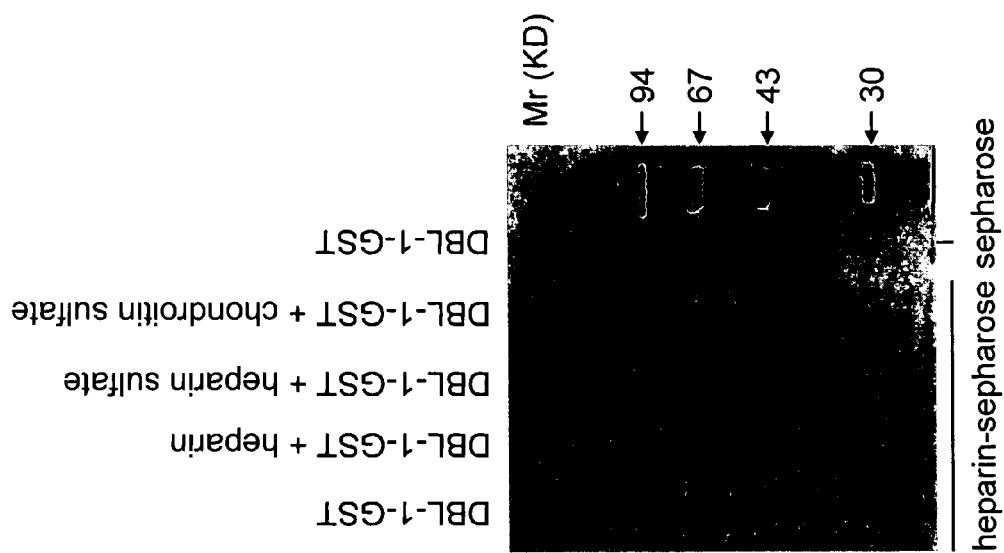
FIG. 3 discloses the binding of rosetting FCR3S1.2-PfEMP1 to heparine as seen by gel analysis of 10% SDS-PAGE stained with Coomassie.
Figure 3B:
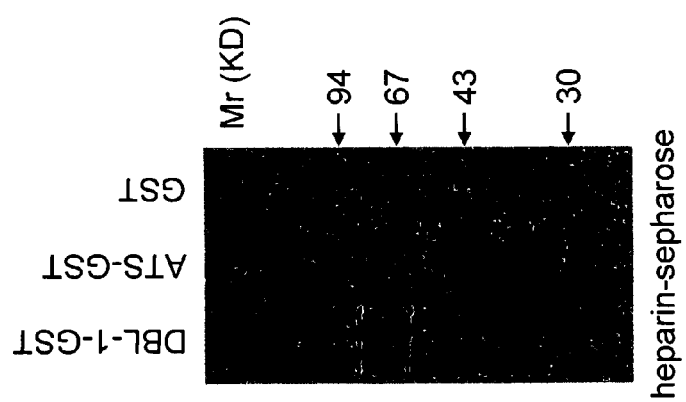
Figure 3A:
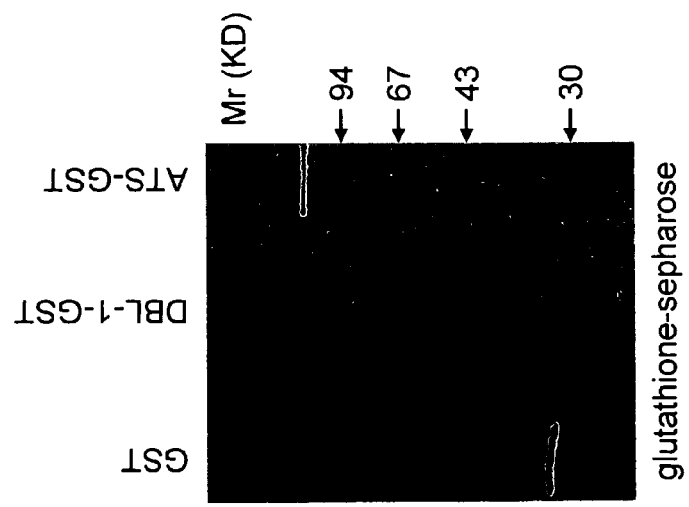

To confirm the above findings experimentally, two domains of the FCR3S1.2-var1 transcript were subsequently expressed: one which had 8 GAG-binding motifs (DBL-1, 1008-bp corresponding to 336 aa) and one which was the highly charged, acidic C-terminal sequence (ATS) that lacks GAG-binding motifs (1353-bp corresponding to 451 aa). The purified DBL-1-GST efficiently bound to heparin-coupled sepharose already after a few minutes at room temperature while the ATS-GST fusion protein did not (FIG. 3B) and a second DBL-1-GST construct covering a distinct var sequence (var 2, Su, X. -Z, V. M. Heatwole, S. P. Wertheimer, F. Guinet, J. A. Herrfeldt, D. S. Peterson, J. A. Ravetch, and T. E. Wellems, 1995. The large diverse gene family var encodes proteins involved in cytoadherence and antigenic variation of *Plasmodium falciparum*-infected erythrocytes. *Cell* 82, 89–100), which lacks GAG-binding motifs, also failed to bind to the heparin-matrix (not shown), The adhesion could dose-dependently be competed out with heparin or heparan sulfate but not with chondroitin sulfate, another negatively charged erythrocyte surface expressed GAG (FIG. 3C). Taken together, this indicates that the binding of DBL-1 to heparan sulfate is dependent on structure and not merely ionic interactions between the two molecules. Heparan sulfate or a heparan sulfate-like GAG therefore seems to be the binding target for the novel PfEMP1-variant.

Rosetting PfEMP1 Binds Directly to Erythrocytes

Figure 3D:
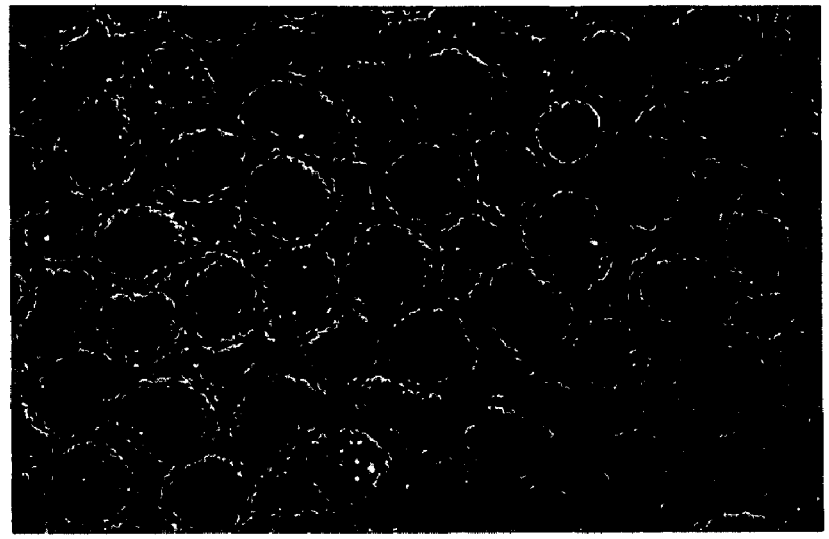
Figure 3E:

To study the potential binding of the recombinant PfEMP1 to erythrocytes we formed monolayers of uninfected erythrocytes on glass-slides. The cells were subsequently incubated with different concentrations of the fusion proteins. While the ATS-GST did not bind to the erythrocytes as detected with an anti-GST mAb, the DBL-1-GST gave a distinct surface staining of all the uninfected erythrocytes (FIGS. 3D, E). This was titratable and could be inhibited with small amounts of heparin or heparan sulfate but not with the related GAG, chondroitin sulfate which suggests that the binding was specific. Heparan sulfate has previously been suggested to be present on human erythrocytes (Trybala, E., B. Svennerholm, T. Bergström, S. Olofsson, S. Jaensson, and J. L. Goodman. 1993. Herpes simplex virus type 1-induced hemagglutination: glycoprotein C mediates virus binding to erythrocyte surface heparan sulfate. *J. Virol.*, 67, 1278–1285, Baggio, B., G. Marzaro, G. Gambaro, F. Marchini, H. E. Williams, and A. Borsatti. 1990. Glycosaminoglycan content, oxalate self-exchange and protein phosphorylation in erythrocytes of patients with idiopathic calcium oxalate nephrolithiasis. Clinical Science, 79, 113–116) and we therefore conclude that the DBL-1-GST fusion protein binds with heparan sulfate specificity to both to the solid-phase matrix as well as to normal erythrocytes.

Recombinant DBL-1 Disrupts Rosettes and Blocks Rosette-Reformation

The effect of the DBL-1 fusion protein on pre-formed rosettes was studied in order to confirm the biological role of PfEMP1 in resetting. Aliquots of a highly rosetting FCR3S1.2 culture was incubated with decreasing concentrations of DBL-1-GST or ATS-GST. DBL-1 caused a dose-dependent rosette reversion with 40–50% reversion at ≈50 µg/ml while the ATS-GST did not show any effect (FIG. 4). The rosettes were not reformed upon prolonged incubation.

Rosetting is Dependent on Heparan Sulfate

Figure 5A:
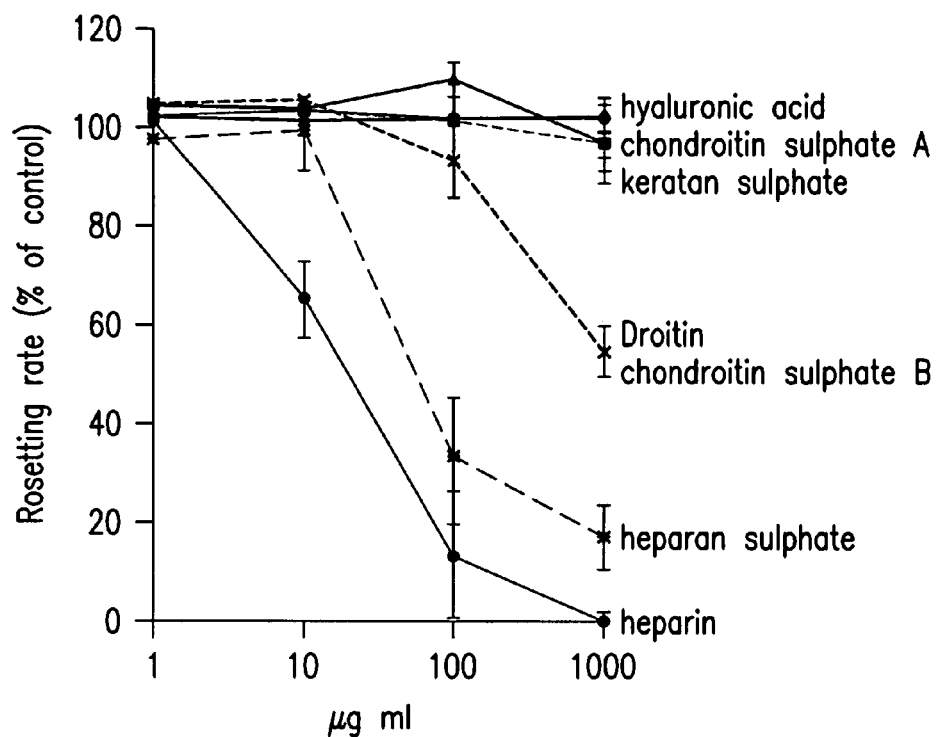
FIG. 5 discloses the effect of glycosaminoglycans on *Plasmodium falciparum* rosetting.
Figure 5B:
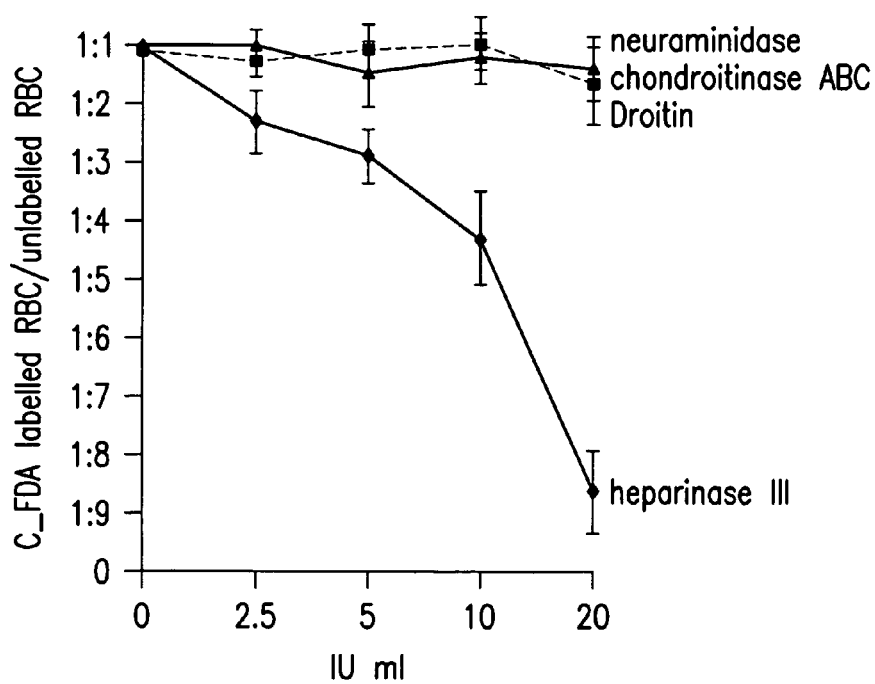

To establish the role of heparan sulfate also in resetting we studied the disruptive activity of different GAGs on FCR3S1.2 rosettes. FCR3S1.2 rosettes were sensitive to both heparin and to heparan sulfate, but neither chondroitin sulfate A, keratan sulfate, nor hyaluronic acid had any effect on the rosettes (FIG. 5A). Chondroitin sulfate B had a slight effect only at high concentrations (FIG. 5A). These findings were confirmed by enzyme treatment of the uninfected erythrocyte heparinase, but not chondroitinase or neuraminidase, treatment blocked the binding (FIG. 5B).

Example 2

Materials and Methods

Parasites and rosetting—Two distinct highly resetting *P. Falciparum* laboratory stains were used: FCR3S1 (previously named R$^+$PA1) and TM 284 (isolated in Thailand, 1990). Parasites were cultivated according to standard procedures (Udomsangpetch et al. 1989). Field isolates were obtained from patients attending the Albert Schweitzer Hospital, Lambaréné, Gabon between April and June 1996. Patients with a *P. falciparum* asexual stage parasite count superior to 10.00/µl blood were included in the study. A venous or capillary blood sample was taken after patients or parents informed consent. Blood was washed three times with RPMI and cultivated according to standard procedures (Udomsangpetch et al. 1989). Assessment for parasite growth and resetting was made every 6–8 hours using a Leitz UV-light microscope. Briefly, an aliquot of parasite culture was mixed with a small amount of acridine orange and the sample was analyzed. Assays were performed on rosetting isolates when the majority of parasites in culture had reached the trophozoite stage. The resetting rate was expressed as the number of infected erythrocytes in rosettes relative to the total number of late stage infected erythrocytes. Three hundred infected cells were counted. Parasitemia was calculated as the number of infected erythrocytes relative to the number of uninfected erythrocytes.

Saccharides—A number of GAGs, polysaccharides, heparin mono- and disaccharides were assessed for rosette disrupting activity. Heparin, heparan sulfate, chondroitin sulfite, dermatan sulfate (all from porcine intestine) as well as fucoidan (*Fucus vesiculosus*), dextran sulfite (Mol. Wt 8.000), keratan sulfate (bovine cornea), hyaluronic acid (rooster comb), heparin/HS mono- and disaccharides (produced by digestion of heparin and HS by various heparinases) were purchased from Sigma (St. Louis, USA). Dextran (Mol. Wt. 60.000) was from Medisan Pharmaceuticals, Stockholm, Sweden. High molecular weight heparin with low affinity for antithrombin III (HMW-LA heparin) was produced by gel filtration of standard heparin on Sephacryl S-200 (Pharmacia, Uppsala, Sweden) followed by passage over an antithrombin-Sepharose 4B column (Carlson et al. 1992). Modification of bovine lung heparin and structural characterizations were performed as described (Feyzi et al. 1997).

Treatment of erythrocytes and infected erythrocytes—Treatments of blood group O Rh$^+$ red blood cells (RBC) and cultures were performed with heparinase III (0.033 IU/ml, 25° C., pH 7,5), chondroitinase ABC (20 IU/ml, 37° C., pH 7,5), *Clostridium perfringens* neuraminidase (0.1 IU/ml, 37° C., pH 6,0) and phospholipase C (0.1 IU/ml, 30° C., pH 7,5). The enzymes were purchased from Sigma and Seikagaku Corporation. Rosetting rate was assessed after 210 minutes incubation with enzyme, without changing any conditions in the culture and was compared to mock treated control cultures. No extracellular parasites or RBC gross morphology change was observed at concentrations and incubation time used. Digestion with trypsin (100 IU/ml, 37° C., pH 7,5) and chymotrypsin (100 IU/ml, 37° C., pH 7,5) was stopped with soybean protease inhibitor (Sigma) after 20 minutes incubation and rosetting rate was assessed. Sodium periodate In RPMI was added to cultures and uninfected RBC at 10 mM concentration. Rosetting rate was checked after 15 minutes incubation at room temperature and compared to mock treated control cultures.

Rosette disruption assays—Assays on wild isolated were performed on cultures presenting a rosetting rate superior to 20% (range 23.6–86.2%, mean 48.6&) and parasitemia 1–10%. For laboratory stains, parasite cultures with rosetting rates of 50–70% and parasitemia 5–8% were used Aliquots (12.5–25 µl) of parasite cultures were mixed with equal amounts of sulfated glycoconjugate compound in RPMI in a 96-well microtiter plate, at final concentrations indicated After incubation for 30 minutes at 37° C. assessment for resetting was made as described above. The resetting rate was compared to that of culture mixed with RPMI.

Competition assay using carboxy-fluorescein diacetate (C-FDA) labelled erythrocytes—In order to measure the relative capacity of treated RBC to form rosettes, a competition assay was performed as described by Carlson and Wahlgren (Carlson et al. 1992), with some modifications. Blood group O $R^+$ RBC were pre-treated for 60–90 min by enzymes or periodate as described above and mixed with a small amount of C-FDA (Sigma) stock solution to a final concentration of 250 µg/ml. The cells were incubated for 10–15 minutes at room temperature, then washed three times with RPMI and finally resuspended at 5% hematocrit in malaria culture medium containing 10% $AB^+$ serum. Controls were mock treated and labelled as described above.

Fresh rosetting cultures grown in blood group O $Rh^+$ RBC from the same donor were resuspended as above. A 25 µl aliquot of culture was mixed with an equal volume of the C-FDA-labelled uninfected RBC that had been subjected to enzyme or periodate pre-treatment The rosettes were disrupted mechanically by drawing the cells through an injection needle (diameter 0.60 mm) 6–8 times. After 30 minutes incubation rosette reformation was assessed and the proportion of labelled to unlabelled RBC in rosettes claculated. Assays were considered valid when the ratio of labelled/unlabelled RBC in the assay was 0.9–1.1 and the ratio of labelled/unlabelled RBC participating in rosettes was 0.9–1.1 for control samples.

Results

Disruption of rosettes from laboratory strains FCR3S1 and TM284 by SGs—Rosette disruption by GAGs and three other related polysaccharides (dextran, dextran sulfate and fucoidan) performed on two laboratory strains revealed differences in GAG-sensitivity (Table I). Although having a similar molecular structure, some compounds totally lacked rosett disrupting activity at high concentrations (1–10 mg/ml), while other compounds were potent rosette disrupters even at lower concentrations (1–10 µg/ml; Table I and not shown). FCR3S1 exhibited high sensitivity for heparin and HS, whereas dermatan/chondroitin sulfate had little or no effect. On the other hand, TM 284 exhibited relatively higher sensitivity for dermatan/chondroitin sulfate than FCR3S1 and was less sensitive to HS/heparin (Table I). Still, heparin disrupten 80%/of TM 284 rosettes at 1 mg/ml (not shown).

Sensitivity of wild isolates to SGs—Thirtytwo patient isolates were characterized in order to analyze the properties of fresh P. Faciparum parasites. The sensitivity of rosettes towards the different GAGs and other sulfated polysaccharides was clearly isolate dependent. In general, two major groups could be discerned (FIG. 1). One group was more sensitive to the glucosaminoglycans heparin and heparan sulfate, and somewhat less to the galactosaminoglycans (chondroitin sulfate and dermatan sulfate). For the second group of isolates the galactosaminoglycans were more effective competitors than the glucosaminoglycans. For both groups, fucoidan was a strong rosette disrupter in contrast to dextran sulfate which was much less effective that GAGs in most of the strains. This picture indicated that charge was an important but not the only determinant in rosette disruption. One the whole collection of wild isolates, fucoidan was the most effective rosette disrupter for most isolates and chondroitin sulfate the least effective, whereas dermatan sulfate, heparin, HS and dextran sulfate had an intermediate position. This was also true at other concentrations tested (10–100 µg/ml; not shown). No clear correlation was observed between differecnes in SG sensitivity of the isolates and parasitemia, rosetting rate or ABO blood group of the patient (not shown).

Disruption of rosettes by modified heparin—In order to investigate the relative importance of different molecular features, modified heparin was tested for rosette disruption on the heparin/HS sensitive FCR3S1 strain. When N-dulfate groups were replaced by the charge neutral acetyl group, heparin was ≃100 fold less efficient in rosetting disruption compared to the native form (FIG. 2). In contrast to this marked effect, O-desulfation seemed to be much less important, as removal of either 2-O- or 6-O-sulfate groups resulted in an ≃10 fold reduction ofd disruption efficiency. Even the most completely O-desulfated sample with only about 30% of disaccharide units still 2-O-sulfated had a similar order of efficiency.

Sensitivity of rosettes to disaccharides—As the effect of heparin seemed to be strongly related tpo the presence of the N-sulfate group, we tested whether the individual disaccharides would have a rosette reverting capacity. Different disaccharides that are gained by heparinase cleavage of heparin and HS were tested in the rosetting assay. The most acitve ones all contained the N-sulfated glucosamine, while the efficiency of the disaccharides was reduced by acetylation of the amino group corroborating data with the modified heparins (FIG. 3). The O-sulfation on the other hand had only limited influence. While 6-O-sulfation seemed to be less important, the 2-O-sulfate had some positive effect in addition to the N-sulfate. Additionally, heparin disaccharides II-H ($\Delta$HexA-GlcN(6-$OSO_3$)), III-H ($\Delta$HexA(2-$OSO_3$-GlcN), and IV-H ($\Delta$HexA-GlcN), all lacking N-sulfation and with a positively charged amino group, exhibited no rosette disrupting effect (not shown).

One active and one inactive disaccharide were studied in detail: complete rosette reversion was obtained by the N-sulfated disaccharide IV-S ($\Delta$HexA-GlcN$SO_3$ at 45 mM while the N-acetylated disaccharide IV-A ($\Delta$HexA-ClcNAc) completely lacked effect (FIG. 4A).

In a preliminary experiment the most predominant heparin disaccharide recovered after heparinase digestion, I-S ($\Delta$HexA(2-$OSO_3$)-GlcN$SO_3$(6-$OSO_3$)), was titrated against heparin for rosette disruption on strain FCR3S1. At a concentration of 30 mM disaccharide, the rosettes were disrupted to the same extent as with heparin at 1 mg/ml (corresponds to ≃70 µM heparin molecules), e.e. the heparin chain was around 20 fold more efficient on a weight basisk and around 500 fold more efficient on a molar basis. When wild type isolates were tested with this concentration of disaccharide, in comparison with the other competitors, it exhibited a similar pattern as heparin (FIG. 1).

Sensitivity of rosettes to monosaccharides—When glucose was tested, the N-sulfated monosaccharides gave −50% rosette reversion at 50 mM and additional sulfite groups and increasing negative charge did not potentiate rosette disruption. Some activity could also be attributed to N-acetylated glucosamine with an O-sulfate ester at C-6 (FIG. 5B). Similar results were obtained when the TM 284 strain was tested, though slightly higher concentrations were required (not shown). Also, N-sulfated galactosamine (not present in any GAG) lacked rosette disrupting activity, whereas N-sulfated glucosamine (common in heparin/HS) caused total rosette disruption (FIG. 4B).

Glycan oxidation and enzymatic treatment of whole cultures—Different treatments of infected erythrocyte cultures caused changes in rosetting behavious withour any gross change on RBC morphology on both strains tested (FIG. 6A). When the cultures were treated with the proteases trypsin or chymotrypsin rosetting was abolished completely, indicating that either receptor or ligand in the adhesion complex is a highly protease-sensitive protein. Heparinase III, which selectively cleaves -4GlcNRα-[1→4]-GlcA1- (where R can be either N-acetamido or N-sulfo) linkages of heparan sulfate chains (Linhardt et al. 1990) resulted in a drastic reduction of the rosetting capacity of FCR3S1 and a somewhat lower decrease of TM 284 rosetting. Chondroitinase ABC, cleaving GalNAcα-[1→4]-GlcA bonds in chondroitin sulfate had only effect on the rosetting of the TM284 strain. No effect was seen by either neuraminidase or phospholipase C treatment. Sodium periodate which would oxidize any glycan type with vicinal hydroxyl groups had an intermediate effect on both parasite stains.

Glycan oxidation and enzymatic treatment of uninfected RBC—In order to assess whether above results can be attributed to the infected RBC per se or to the uninfected RBC that participate in resetting, competition assays were achieved wioth pre-treated, C-FDA labelled uninfected RBC. Sodium peri date treatment of uninfected RBC decreased their rosette binding capacity 4 tim s compared to non-treated RBC. The rosette binding capacity of heparinase m treated RBC was also deceased 4–5 fold.

Treatment with heparinase III in presence of soybean protease inhibitor did not reverse the effect, and addition of HS to heparinase completely blocked the heparinase activity (not shown). Also, typsin and chymotrypsin treatment affected the binding capacity, with a 2–5 fold decrease, but less than the treatment of the whole culture. This finding suggests that the primary protease sensitive molecule is the ligand on the infected RBC, while not all receptor structures on the uninfected RBC are sensitive to proteolytic degradation. This can be either due to a reduced protease sensitivity of glycosylated proteins/proteoglycans or because the receptor glycans would sit on a non-proteinaceous core. For the TM 284 strain, a two fold decrease of binding capacity was observed after chondroitinase ABC treatment, whereas FCR3S1 was unaffected (FIG. 6 B).

DISCUSSION

The present invention discloses the identification of a novel PfEMP1-variant as the rosetting ligand and heparan sulfate, or a heparan sulfate like molecule, as the rosetting receptor. A single cell RT-PCR technique was developed in order to investigate the association of expression of the novel PfEMP1-variant with rosetting-binding at the single cell level. The PfEMP 1 messages were found to be present in ring stage parasites, in trophozoites and in schizonts, although it was less abundant in the more mature stage parasites. However, these were studied in great detail as they do form rosettes and rings do not. One PfEMP 1 mRNA species was amplified from single rosetting parasites and the appearance of the same fragment in amplifications with total RNA from R$^+$ bulk cultures, but not with total RNA from non- or low resetting parasites, indicated that the message was unique to resetting parasites. It was evident, however, that the parasites were not homogeneous even in cultures of a high resetting rate suggesting that the non-rosetting parasites may express different PfEMP 1s. Similarly, although a strong hybridisation to a ≈7.5 kb message from the resetting parasites was found, there was still a small hybridisation to a slightly smaller species with RNA from the R$^-$ parasites. This probably reflects the transcription of a different var gene, since the FCR1S.2 var1 sequence was not found in the amplified products from R– parasites.

Cloning of full length cDNA from eukaryotic cells is always difficult. For example, an et al. (1995) Hum. Mol. Genet. 4: 1259–1266, have shown that different methods of identifying cDNAs from a genomic region result in a surprisingly different array of candidate genes. To be able to achieve this, the RT-PCR parameters were first optimised, so that most PfEMP 1 transcripts could be amplified. With these conditions and a primer sequence from the unique 434-bp rosetting PfEMP1 cDNA, one large single down-stream fragment of 4.9-kb of cDNA was amplified, which upon the digestion with EcoR I and Hind III was fragmented into distinct bands indicating that the amplified product was composed of one sequence. The 4.9-kb cDNA species was subsequently confirmed to be a single amplificate by sequencing. Rosetting-PfEMP1 specific sequences of both the variable region, upstream to the trans-membrane domain, and of the 434-bp fragment were used to obtain the sequences of overlapping regions of the 3' and the 5' regions of his transcript Five overlapping fragments were sequenced to ascertain the 3' overlap and seven to ascertain the 5' overlap. The correctness was further checked by RT-PCR with specific primers flanking the overlapping regions after the assembly of the entire coding sequence. Each of the 14 PCR-amplified fragments were sequenced in both directions and the overlapping fragments were found to be correct and identical in all regions. It is therefore, hypothesized that the assembled transcript is indeed derived from one single gene.

The high sensitivity of rosettes to heparin and above specified glycosamino glycans (GAGs) made the present inventors speculate that the parasite uses sulfated carbohydrates as the rosetting receptor. The appearance of potential GAG binding motifs in this novel PfEMP 1 sequence was therefore checked after the assembly of the transcript. Clusters of GAG binding motif, the consensus sequence of which have previously been proposed by others, were then identified. All the motifs showed an identical or a similar composition as other published heparin or heparan sulfate binding motifs found in both malaria parasites and other orgasms (Sinnis, P., P. Clavijo, D. Fenyö, B. T. Chait, C. Cerami, and V. Nussenzweig. 1994. Structural and functional properties of region II-plus of the malaria circumsporozoite protein. J. Exp. Med. 180, 297–306, Jackson, L. R., J. S. Busch, and D. A. Cardin. 1991. Glycosaminoglycans: molecular properties, protein interactions, and role in physiological processes. Physiol. Rev., 71, 481–530). The expressed DBL-1, which had 8 motifs, bound to heparine-sepharose, to the membrane of normal RBC, disrupted naturally formed rosettes and blocked rosette-reformation while the ATS fusion protein did not. The inhibitory activity of heparan sulfate as well as the inability of chondroitin sulfate to inhibit or block the attachment informed us that it was the molecular structure of the GAG that is important for binding. In complementary experiments, the DBL-1 region of a second var-gene transcript (var-2) which lacks GAG-binding motifs was expressed and found to bind to the heparin-sepharose (Sahlen, not shown), which also support a functional role of the GAG binding sequences in the rosetting DBL-1.

The rosette reversion obtained by the addition of recombinant DBL-1 to naturally formed rosettes indicated that the parasite uses the novel PfEMP1-variant as the main rosetting ligand. The deletion of rosetting by heparinase treatment of normal RBC provided further confirmation about this specific ligand-receptor interaction, indeed suggesting that heparan sulfate, or at least a heparan sulfate-like molecule, is involved in the binding. Heparinase treatment also disrupted the rosettes of other strains of parasites (TM180, TM284), while the rosettes of the strain R29 were not affected (not shown), findings which are in concordance with those of Rowe et al (Rowe, J. A., J. M. Moulds, C. I. Newbold, and L. H. Miller. 1997. *P. falciparum* resetting mediated by a parasite-variant erythrocyte membrane protein and complement-receptor 1. *Nature* 388:292–295). In separate experiments, heparin-derived mono- and di-saccharides which were of the same net charge but had their sulfate groups at different positions were studied for their rosette-disrupting activities. Those with the sulfate groups in the same position as heparan sulfate inhibited binding while the others did not (Barragan unpublished and see above). Further, while the N-sulfated mono-saccharide glucosamine, a component of heparan sulfate, had a good anti-rosetting activity the identically N-sulfated galactosamine had none (Barragan et al, unpublished). Heparin has also been found to disrupt rosettes from 27 out of 54 fresh *P. falciparum*-isolates (50%) suggesting that heparan sulfate is used by these parasites as rosetting receptors (Carlson, J., H. P. Ekre, H. Helmby, J. Gysin, B. M. Greenwood, and M. Wahlgren. 1992. Disruption of *Plasmodium falciparum* erythrocyte rosettes by standard heparin and heparin devoid of anticoagulant activity. *Am. J. Trop. Med. Hyg.* 46, 595–602). The receptors used by the heparin-resistant fresh isolates maybe other GAGs, as it has been found that rosettes of most parasites may be disrupted by either one or the other of the human GAGs (Barragan, unpublished), Further, other sulphated glycans, such as fucoidan, disrupted rosettes of almost all fresh isolates (FIG. 1). Thus, according to the present invention, it has been found that FCR3S1.2 uses heparan sulfate, or a heparan sulfite like molecule, on the erythrocyte surface as a rosetting receptor and that the other GAGs may be receptors of other parasites.

Heparan sulfate is a molecule presents on all cells, including erythrocytes (Trybala, E., B. Svennerholm, T. Bergström, S. Olofsson, S. Jaensson, and J. L. Goodman. 1993. Herpes simplex virus type 1-induced hemagglutination: glycoprotein C mediates virus binding to erythrocyte surface heparan sulfate. *J. Virol.*, 67, 1278–1285, Baggio, B., G. Marzaro, G. Gambaro, F. Marchini, H. E. Williams, and A. Borsatti. 1990. Glycosaminoglycan content, oxalate self-exchange and protein phosphorylation in erythrocytes of patients with idiopathic calcium oxalate nephrolithiasis. Clinical Science, 79, 113–116); $4 \times 10^6$ molecules have been suggested to be expressed at the surface of normal hepatocytes (Kjellen, L., A. Oldberg, and M. Höök. 1980. Cell surface heparan sulfate. J Biol. Chem. 21, 10407–10413). The density on the RBC should also be high if this indeed is the receptor used by the parasite for rosetting. The involvement of GAGs as receptor structures for other cell-to-cell interactions of *P. falciparum* has previously been suggested e.g. for endothelial binding, for liver- and erythrocyte invasion (Sinnis, P., P. Clavijo, D. Fenyö, B. T. Chait, C. Cerami, and V. Nussenzweig. 1994. Structural and functional properties of region II-plus of the malaria circumsporozoite protein *J. Exp. Med.* 180, 297–306, Kulane, A., H -P. Ekre, P. Perlmann, L. Rombo, M. Wahlgren, and B. Wahlin. 1992. Effect of different fractions of heparin on *Plasmodium falciparum* merozoite invasion of red blood cells in vitro. *Am. J. Trop. Med. Hyg.*, 46, 589–594, Robert, C., B. Pouvelle, P. Meyer, K. Muanza, A. Scerf, and J. Gysin. 1995. Chondroitin-4-sulfate (proteoglycan) as *Plasmodium falciparum*-infected erythrocyte adherence receptor of brain microvascular endothelial cells. *Res. Immunol.* 146, 383–393, Rogerson, S. L, S. C. Chaiyaroj, K. Ng, J. C. Reeder, and G. V. Brown. 1995. Chondritin sulfate A is a cell surface receptor for *Plasmodium falciparum*-infected erythrocytes. *J. Exp. Med.* 182, 15–20). Taken together this may indicate that the parasite has adapted a more general strategy for interacting with the host by using the negatively charged proteoglycans as receptors exposed on the exterior of every cell surface.

According to the present invention, it has also been found that the rosette disruption capacity is not only determined by the molecular weight of SGs. Hyaluronic acid, by far the largest of all tested molecules, exhibited no rosette disrupting activity while smaller molecules did Also, an association between average negative charge and rosette reverting capacity was not always observed, e.g. hyaluronic acid which has a higher average negative charge density than fucoidan did not exhibit a rosette-disrupting activity while fucoidan did. Comparison of heparin and fucoidan, on the other hand, suggests that the effect of correct positioning within a three dimensional structure could be much more essential than the average amount of negative charge which is clearly lower in fucoidan (Patankar et al. 1993). An association to negative charge could be the explanation for differences between heparin and HS, although more specific sequence determinants can not be excluded.

When assaying the heparin/HS-sensitive FCR3S1 strain it is apparent that modified heparin preparations with reduced overall degree of sulfation, and thus negative charge, loose competition capacity though not in a strictly charge dependent manner. This finding supports the conclusion that other determinants must be of importance for the binding to infected erythrocytes. N-desulfated heparin preparations were at least one hundred times weaker rosette reverters comparted to heparin. In contrast to the effect of N-desulfation, O-desulfation seemed to be connected with minor reduction of competition efficiency, indicating the importance of the type of sulfate, i.e. N-sulfation. An analogous conclusion may be drawn by comparison of the more efficient rosetting reverter heparin as compared to HS. One of the basic differences between heparin and HS is the degree and distribution of the N-sulfate groups, which in turn leads to a predominant localization of O-sulfation to N-sulfated blocks (Salmivirta et al. 1996). N-sulfation reaches 40–60% of all the disaccharides in an average HS chain (Maccarana et al. 1996) while the value for heparin is over 90%. Indeed, the difference in competition offect of heparin and HIS in rosetting could be explained by the more abundant presence of N-sulfation in heparin.

To further test the importance of sulfation position over anionic feature of a carbohydrate, heparin/HS derived mono- and disaccharides were assayed for rosette disrupting activity. Twenty-nine wild isolates were tested for sensitivity to heparin and heparin disaccharide I-S (ΔHexA(2-OSO$_3$)-GlcNSO$_3$-(6-OSO$_3$)), and the sensitivity pattern obtained was very similar for the two compounds at equipotent concentrations, whereas it could differ for other GAGs and polysaccharides. Our results talk therefore in favour of an identical site of action for heparin and the heparin disaccharide I-S suggesting that results with mono- and disaccharides reflect at least part of the heparin HS binding site(s) on infected erythrocytes.

Molecular net negative charge can not by itself explain the anti-rosetting activity: some highly negatively charged monosaccharides exhibited no rosette disrupting effect, while some monosaccharides with one single negative charge disrupted rosettes. Also, the fact that higher degree of sulfation did not increase rosette reverting potency, corroborates that it is the position of the sulfate group(s) rather than the number that is the determinate. In case of the disaccharides, 6-O-sulfation seems to be less important, while the 2-O-sulfate has some positive effect in addition to the N-sulfate group. This could be explained by rotational freedom of the glycosidic linkage which results in the possible exposure of both sulfate groups on the same side of the sugar plane, while the 6-O-sulfate would protrude on the opposite side. Also, N-sulfated glucosamine (present in heparin and HS) abolishes rosetting, whereas its stereoisomer N-sulfated galactosamine (not present in any GAG) does not, all emphasizing that the N-sulfated glucosamine is part of the binding sequence.

To analyze whether competition by heparin and heparin derived oligosaccharides reflects the existence of a heparin/HS-like ligand on the erythrocytes, whole cultures and uninfected erythrocytes were treated by different glycan degrading procedures. For the heparin/HS sensitive strain FCR3S1 a clear reduction of rosette formation was provoked by either unspecific glycan oxidation through periodate or a selective digestion of heparin/HS chains by heparinase (FIG. 6). Rosetting was not hampered by either chondroitinase, neuraminidase or phospholipase C treatment of cultures, supporting the view that the ligand is of heparin/HS nature. Proteolytic treatment of the cultures, on the other hand, indicated that protein components are involved in the rosetting mechanism as well, either as lectin-lika ligands (i.e. on the infected erythrocyte) or as carrier of the glycan epitopes (i.e. on the uninfected erythrocyte). Rosetting by strain TM 284 seemed to be more sensitive to competition by chondroitin sulfate and dermatan sulfate, although higher amounts of heparin/HS were also effective. This observation was confirmed by enzymatic treatment of the erythrocytes as chondroitinase had a profound effect on the rosetting.

The separate treatment of uninfected erythocytes was performed in order to establish whether the infected erythrocyte or the rosetting uninfected erythrocytes contain specific features involved in rosetting. The higher sensitivity of the uninfected erythrocytes for glycan destruction would indicate that glycan structures constitute parts of the rosetting receptor(s). The opposite argumentation would hold true for the proteolytically destroyed component which seems to sit on the side of the infected erythrocytes, although also a part of the glycans could be removed by proteolytic cleavage of their core proteins. However, the infected erythrocytes seem to be much more sensitive for the proteolytic degradation as compared to glycan oxidation.

We have previously suggested that rosetting may be mediated by lectin-like interactions, with non-obligate involvement of different ABO-blood group antigens (Carlson et al. 1992). CD36 has also been attributed a receptor function (Handunnetti et al. 1992) and recently, complementreceptor 1 was reported to play a role in the fomration of rosettes (Rowe et al. 1997). The fact that heparin sensitivity decreases when the same parasites are cultivated in erythrocytes from their preferred ABO-blood group (Carlson et al. 1992) could indicate simultaneous involvement of more than one rosetting receptor and that heparin is not interacting with these receptors. A role for serum proteins in rosetting has also been shown (Scholander et al. 1996). Although an interaction of GAGs with serum factors can not be excluded, this effect should be of minor importance since strains with different serum dependency were equally affected (not shown). Furthermore, a recombinant fusion-protein covering the C-terminally located Duffy-like binding domain (DBL-1) of PfEMP1, adhered directly to erythrocytes and bound to a heparin-matrix, in the absence of serum factors (Chen et al. 1998).

As a conclusion, the present invention provides the identification, by single-cell RT-PCR and cDNA cloning, of a new adhesive ligand *Plasmodium falciparum* erythrocyte membrane protein-1-variant, PfEMP1. Rosettes of the novel PfEMP1-variant contains clusters of glycosaminoglycan-binding motifs. A recombinant fusion protein (DBL-1-GST) has been found to adhere directly to normal erythrocytes, disrupt naturally formed rosettes, block rosette-reformation and bind to a heparin-sepharose matrix. The adhesive interactions could be inhibited with heparan sulphate or enzymes that remove heparan sulfate from the cell surface while other enzymes or similar glycosaminoglycans of an alike negative charge did not affect the binding. Further, fucoidan, a sulfated glycan, has been shown to be particularly effective in disrupting rosettes. The novel PfEMP1-variant is suggested to be the rosetting ligand and carbohydrates, heparan sulfate, or a heparan sulfate-like molecule, the receptor both for PfEMP1 binding and naturally formed erythrocyte rosettes.

The invention claimed is:

1. An isolated polypeptide comprising SEQ ID NO: 1.
2. An isolated polypeptide consisting of SEQ ID NO: 1.
3. An isolated polypeptide comprising amino acids 79–415 of SEQ ID NO: 1, and wherein SEQ ID NO:1 is a *plasmodium* erythrocyte membrane protein (PfEMP1) polypeptide.
4. An isolated polypeptide consisting of amino acids 79–415 of SEQ ID NO: 1, and wherein SEQ ID NO:1 is a *plasmodium* erythrocyte membrane protein (PfEMP1) polypeptide.
5. The isolated polypeptide according to claim 3, wherein said polypeptide binds to a negatively charged heparan sulfate and heparan sulfate-like molecule.
6. The isolated polypeptide according to claim 4, wherein said polypeptide binds to a negatively charged heparan sulfate and heparan sulfate-like molecule.

* * * * *